United States Patent
Manyak et al.

(10) Patent No.: US 6,759,040 B1
(45) Date of Patent: Jul. 6, 2004

(54) PREPARATION AND USE OF BIOFILM-DEGRADING, MULTIPLE-SPECIFICITY, HYDROLYTIC ENZYME MIXTURES

(75) Inventors: David M. Manyak, Ellicot City, MD (US); Ronald M. Weiner, Potomac, MD (US); Peter S. Carlson, Chevy Chase, MD (US); Ernesto J. Quintero, San Francisco (PA)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 09/508,431
(22) PCT Filed: Sep. 11, 1998
(86) PCT No.: PCT/US98/18167
§ 371 (c)(1),
(2), (4) Date: Aug. 10, 2000
(87) PCT Pub. No.: WO99/14312
PCT Pub. Date: Mar. 25, 1999

Related U.S. Application Data

(60) Provisional application No. 60/058,855, filed on Sep. 12, 1997, and provisional application No. 60/058,856, filed on Sep. 12, 1997.

(51) Int. Cl.[7] .............................................. A61K 38/46
(52) U.S. Cl. ...................... 424/94.2; 424/94.6; 435/264
(58) Field of Search ................................ 435/264, 195; 424/94.6, 94.2, 93.4

(56) References Cited

U.S. PATENT DOCUMENTS

| | | | | |
|---|---|---|---|---|
| 4,144,327 A | * | 3/1979 | Davies et al. ............... | 424/94.2 |
| 4,144,354 A | * | 3/1979 | Unno et al. ..................... | 426/2 |
| 4,335,101 A | * | 6/1982 | Stoudt et al. .................. | 424/50 |
| 4,936,994 A | * | 6/1990 | Wiatr .......................... | 210/632 |
| 5,418,156 A | * | 5/1995 | Stosz et al. ................. | 435/68.1 |
| 5,582,825 A | * | 12/1996 | Sakaguchi et al. .......... | 424/94.5 |

* cited by examiner

Primary Examiner—Jean C. Witz
(74) Attorney, Agent, or Firm—Arent Fox Kintner Plotkin & Kahn PLLC

(57) ABSTRACT

The present invention is directed to the production and use of custom tailored, bacterial enzyme mixtures or components thereof for degrading biofilms in both industrial and therapeutic applications. The industrial applications include but are not limited to the use biofilm-degrading, multiple specificity, hydrolytic enzyme mixtures for removing or preventing the formation of biofilms in water cooling towers, industrial process piping, heat exchangers, in food processing or food preparation, in potable water systems, reservoirs, swimming pools, or related sanitary water systems, and on membranes such as those used for desalinization, industrial processes, or related applications. The therapeutic applications include but are not limited to the use of therapeutically-useful, multiple-specificity, hydrolytic enzyme mixtures for the prevention or treatment of dental caries, periodontal disease, cystic fibrosis or the complications or symptoms of cystic fibrosis, removal of biofilms from contact lenses, and diseases or complications associated with biofilm formation on implantable medical devices such as cardiovascular devices.

35 Claims, 8 Drawing Sheets

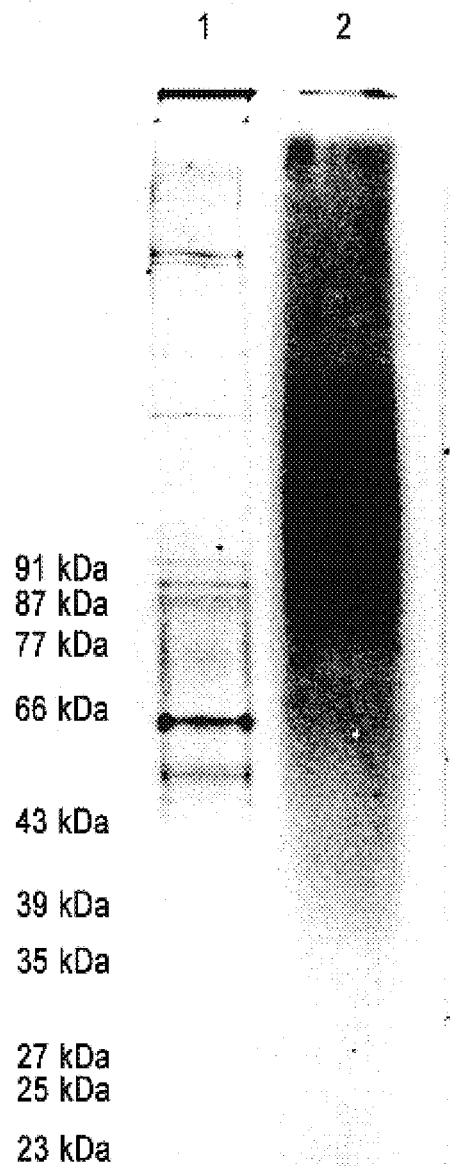
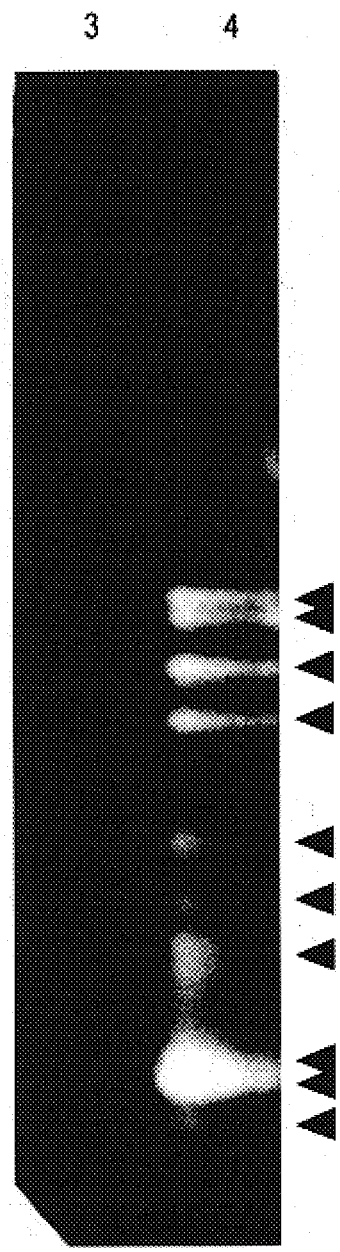
Fig.7A SILVER STAIN
Fig.7B ZYMOGRAM

Fig.8

```
   1  AGCAGTGGGA ATATTGCACA ATGGGCGAAA GCCTGATGCA GCCATGCCGC
  51  GTGTGTGAAG AAGGCTTTCG GGTTGTAAAG CACTTTCAGT AGGGAGGAAA
 101  GGTTAGTAGT TAATACCTGC TAGCTGTGAC GTTACCTACA GAAGAAGCAC
 151  CGGCTAACTC CGTGCCAGCA GCCGCGGGTAA TACGGAGGGT GCAAGCGTTA
 201  ATCGGAATTA CTGGGCGTAA AGCGCGCGTA GGCGGTTAGC TAAGCTAGAT
 251  GTGAAAGCCC AGGGCTTAAC CTTGGAACTG CATTTAGAAC TGGTTGACTA
 301  GAGTATGGTA GAGGGTGTG GAATTTCAGG TGTAGCGGTG AAATGCGTAG
 351  AGATTTGAAG GAACATCAGT GGCGAAGGCG ACACCCTGGA CCAATACTGA
 401  CGCTGAGGTG CGAAAGCGTG GGGAGCAAAC AGGATTAGAT ACCCTGGTAG
 451  TCCACGCCGT AAACGATGTC TACTAGCCGT TGGGGTCCTT GAGGCCTTAG
 501  TGGCGCAGCT AACGCACTAA GTAGACCGCC TGGGGAGTAC GGCCGCAAGG
 551  TTAAAACTCA AATGAATTGA CGGGGGCCCG CACAAGCGGT GGAGCATGTG
 601  GTTTAATTCG AAGCAACGCG AAGAACCTTA CCAGGTCTTG ACATCCAGAG
 651  AACTTACTAG AAATAGTTTG GTGCCTTCGG GAACTCTGAG ACAGGTGCTG
 701  CATGGCTGTC GTCAGCTCGT GTCGTGAGAT GTTGGGTTAA GTCCCGTAAC
 751  GAGCGCAACC CTTGTCCTTA GTTGCTAGCA GGTAATGCTG AGAACTCTAA
 801  GGAGACTGCC GGTGACAAAC CGGAAGAAGG TGGGGACGAC GTCAAGTCAT
 851  CATGGCCCTT ACGACCTGGG CTACACACGT GCTACAATGG CCATAAAACT
 901  GGGTTGCCAA GCCGCGAGGT GGAGCTAATC CCATAAAACT GATCGTAGTC
 951  CGGATTGGAG TCTGCAACTC GACTCCATGA AGTCGGAATC GCTAGTAATC
1001  GTGAATCAGA ATGTCACGGT GAATACGTTC CCGGGCCTTG TACACACCGC
1051  CCGTCACACC ATGGGAATGG GTTGCACCAA AAATTACTAA TCTAACCTTC
1101  GGGGGACGG TTACCACGGT GTGATTCATG A
```

PREPARATION AND USE OF BIOFILM-DEGRADING, MULTIPLE-SPECIFICITY, HYDROLYTIC ENZYME MIXTURES

This is a 371 of International Application Ser. No. PCT/US98/18167 filed on Sep. 11, 1998, which is based on U.S. Provisional Application Ser. No. 60/058,855, filed on Sep. 12, 1997 and U.S. Provisional Application Ser. No. 60/058,856, filed Sep. 12, 1997.

FIELD OF THE INVENTION

The present invention relates to a method for preparing biofilm degrading, multiple specificity, hydrolytic enzyme mixtures which are specifically tailored to remove targeted biofilms. The present invention also is directed to methods for using hydrolytic enzyme mixtures in both industrial and therapeutic applications. The industrial applications include but are not limited to the use of biofilm-degrading, multiple specificity, hydrolytic enzyme mixtures for removing or preventing the formation of biofilms in water cooling towers, industrial process piping, heat exchangers, in food processing or food preparation, in potable water systems, reservoirs, swimming pools, or related sanitary water systems, and on membranes such as those used for desalinization, industrial processes, or related applications.

The therapeutic applications include but are not limited to the use of therapeutically-useful, multiple-specificity, hydrolytic enzyme mixtures or components thereof for the prevention or treatment of dental caries and periodontal disease, improving the treatment of cystic fibrosis or the complications or symptoms of cystic fibrosis, and diseases or complications associated with biofilm formation on implantable medical devices such as cardiovascular devices. The route of administration can be by any means including delivering the hydrolytic enzyme mixture by aerosol to the lungs and applying the hydrolytic enzyme mixture topically.

BACKGROUND OF THE INVENTION

Naturally occurring biofilms are continuously produced and often accumulate on numerous industrial surfaces and on biological surfaces. In an industrial setting, the presence of these biofilms causes a decrease in the efficiency of industrial machinery, requires increased maintenance, and presents potential health hazards. For example, the surfaces of water cooling towers become increasingly coated with microbially produced biofilm slime which both constricts water flow and reduces heat exchange capacity. Water cooling tower biofilms may also harbor pathogenic microorganisms such as *Legionella pneumophila*. Food preparation lines are routinely plagued by biofilm build-up both on the machinery and on the food product where biofilms often include potential pathogens. Industrial biofilms are complex assemblages of insoluble polysaccharide-rich biopolymers which are produced and elaborated by surface dwelling microorganisms. The chemical composition of industrial biofilms are diverse and are specific to each species of surface dwelling microorganism. Because of this complexity and diversity, non-specific hydrolytic enzymes are ineffective in degrading these biofilms and consequently ineffective in reducing or eliminating the undesirable biofilm.

On a biological surface, the presence of these biofilms results in the growth of, and subsequent colonization by, pathogenic microorganisms on an internal or external surface of a host animal or on the surface of objects introduced into the animal (e.g surgical implants). Animal pathogens which colonize surfaces are often maintained and protected by unique polysaccharide rich biofilms produced by the pathogen. Such biofilms coat the infected or colonized surface of the animal or implanted object and continue to be produced during the disease process. For many diseases, biofilms are required for the disease process to become established and to progress. The chemical compositions of pathogen-associated surface biofilms, which consist of complex mixtures of biopolymers, are specific to each species of pathogen. Because of this complexity, non-specific hydrolytic enzymes or hydrolytic enzymes with a single specificity are ineffective in degrading these biofilms and consequently ineffective in reducing or eliminating the disease condition. At the present time, there are no therapeutic products which are commercially employed to degrade and remove these disease related, pathogen-produced biofilms.

Currently, biofilms are most commonly removed using physical abrasion a process which is both inefficient and incomplete. Antimicrobials (biocides and antibiotics) are employed to slow biofilm build-up by killing the microbes that produce biofilms; however, once established, the biofilms protect the embedded, biofilm-producing bacteria from the action of these agents. Furthermore, many antimicrobial agents are toxic and damaging to the environment. Consequently, there is a need for a method to readily remove and control biofilms that does not depend solely on physical abrasion or on the action of antimicrobial agents. This need could be met by a mixture of multiple specificity, hydrolytic enzymes which have been tailored to degrade the specific complex biopolymer composition of a target biofilm. A tailored mixture of multiple hydrolytic enzymes could be employed to degrade biofilms resulting in their more complete removal and in enhanced antimicrobial activity.

It has recently become apparent that insoluble complex polysaccharides (ICP) in the environment are most efficiently degraded by a cascade of enzymes acting in concert. The degradation of these insoluble complex polysaccharides require more than "simple" exoenzymes. Normally, an array of enzymes, part of a complex system, is required to fully hydrolyze the polysaccharide into its final monosaccharide end product (Belas et al., 1988; Bassler et al., 1991b; Bayer & Lamed 1992; Salyers et al., 1996; Svitil et al., 1997). Most of the carbohydrate-degrading enzymes are highly specific for glycosidic sugar and the anomeric configuration of the glycosidic bond. They can act endolytically, hydrolyzing internal carbohydrate bonds, generating oligosaccharide intermediates resulting in relatively rapid viscosity decreases of the polymer; others act exolytically, degrading the polymer from the non-reducing termini generating a single monosaccharide end product. These enzymes tend to show a higher specificity with high molecular weight substrates than lower molecular weight substrates.

For the degradation of the insoluble complex polysaccharides, enzyme localization relative to other enzymes and biomolecules is often important for enzyme efficiency, as is the chemistry of its active site. Many reports have been published describing the properties of numerous isolated polysaccharide-degrading bacteria; however, relatively little is understood concerning how intact bacteria degrade insoluble complex polysaccharides or how the multiple enzymes produced by the organism interact (Salyers et al., 1996). It should be noted that degradation of the insoluble complex polysaccharides into its monosaccharide requires multiple enzymes and possibly other proteins (e.g. substrate-binding).

The present invention teaches general methods for preparing biofilm-degrading, multiple-specificity hydrolytic enzyme mixtures which are specifically tailored to remove targeted industrial and/or disease-related biofilms. These biofilm degrading hydrolytic enzyme mixtures can be employed to remove or degrade biofilms from the target surface causing a reduction of the biofilm and resulting in increased efficiency and improved hygiene in industrial settings and in improved treatment in therapeutic settings. The present invention will find application in numerous settings where biofilms currently present efficiency and health problems.

Hydrolytic enzyme mixtures can be employed, via direct application to the biofilm, to remove or degrade disease-associated and/or industrial biofilms from the surfaces colonized by the pathogen. The present invention will find application in industrial settings, such as water cooling towers, waste water piping, heat exchangers, and food preparation lines. The present invention will also find application as a therapeutic agent for the treatment of numerous currently uncontrolled animal, and particularly human, diseases. For example: i) Oral plaque-forming bacterial species, the causal agents of dental caries, are maintained by complex biofilms required for their continued colonization of the tooth surface and their disease causing action. Animal species, particularly humans, exposed to these oral plaque-forming bacteria are at risk of developing caries. These pathogen-related biofilms are currently removed by physical abrasion. ii) *Porphyromonas gingivalis*, the causal agent of periodontal disease, requires a glycocalyx biofilm for its disease action. Human periodontal disease is currently the major cause of tooth loss world-wide. iii) Cystic fibrosis, which has a frequency of 1 in every 2,000 live births, frequently is associated with infection by *Pseudomonas aeruginpsa* in the lungs, *P. aeruginosa* produces a complex, alginate-based biofilm which directly results in the hyper-viscous mucus characteristic of cystic fibrosis patients. This biofilm is also the substrate for pulmonary infections by opportunistic pathogens characteristic of the disease. iv) Implantable medical devices, such as artificial valves, stents, and catheters, can become colonized by pathogens such as Streptococcus sp., leading to premature failure of the devices and/or life-threatening secondary infections. v) contact lenses can become coated with biofilms and colonized by pathogens. The enzyme mixtures of the present invention will conveniently remove these biofilms.

Microorganisms which degrade complex polysaccharides are known in the art. Some marine microorganisms faced with oligotrophic conditions in the pelagic zone, have evolved powerful enzyme systems to take advantage of the ubiquitous marine snow, which are potential oases in the nutritionally poor open waters. As a consequence, selected marine species have developed very efficient mechanisms to utilize complex polysaccharides. Marine bacterium Microbulbifer [e.g. 2–40 (deposited at the American Type Culture Collection as ATCC 43961) and IRE-31 (deposited at the American Type Culture Collection as ATCC 700072)] and Marinobacterium [e.g. KW40 (deposited at the American Type Culture Collection as ATCC 700074)] have been identified as a potentially important bioremediation species, since they synthesize an unusually large number of degradative enzymes. Marine bacterium Microbulbifer 240 is described in U.S. Pat. No, 5,418,156 (described as Alteromonas 2–40 in U.S. Pat. No. 5,418,156 but subsequently determined through nucleic acid sequencing to be a Microbulbifer) which is hereby incorporated by reference into the present document. The marine/estuarine bacterium, 2–40, is a periphytic organism isolated from a salt marsh growing on *Spartina alterniflora*. It is Gram negative, pleomorphic, rod-shaped and motile. This aerobe requires sea salts and carbohydrates for growth. It produces numerous proteases, lipases, and carbohydrases that allow Microbulbifer to degrade a variety of complex, insoluble polysaccharides of plant, fungi, and animal origin. These polysaccharides include alginate, araban, carrageenan, carboxymethylcellulose, chitin, glycogen, $\beta$-glucan, pectin, laminarin, pullulan, starch, xylan, and agar.

Relatively recently, a novel structure relating to insoluble substrate degradation was discovered in a Gram positive bacterium. It was a cellulose-binding and multicellulase-containing cell-surface protuberance produced by *Clostridium thermocellum* and *C. cellulovorans*. Coined "cellulosomes" they were found to attach directly to the insoluble substrates, via special cellulose binding proteins. Thus, they bring cellulases into contact with cellulose, targeting the enzyme substrate complex. Cellulosomes are comprised of at least 14 different proteins. Cip A refers to the largest of the cellulosome proteins, approximately 250 kDa. It serves as the scaffolding protein, binding and anchoring the enzymatic components and securing the entire cellulosome on the cell surface. This protein has a 166 amino acid sequence that is repeated 9 times and is a receptor for the enzymatic cellulosome components, such as CeID. CeID is a 68 kDa endoglucanase isolated from the cellulosome whose carboxy-terminus has a docking sequence that binds to the CipA receptors.

Such structures (hereinafter "degradosomes") may be involved in the depolymerization of other insoluble polymers in addition to cellulose. Degradosome components could also consist of spatially arrayed enzymes, adhesions and scaffold protein. Not only do degradosomes maintain the released monomer product close to the cell for metabolic utilization, but the degradosome may place a cascade of hydrolytic enzymes in proper juxtaposition for optimal enzyme activity. It is also an attachment organelle, incorporating specific polymer binding proteins. Because of whole cell/degradosome efficiency and the potential for continued enzyme synthesis, the use of living bacteria as bioreactors in the degradation of not only cellulose, but also potential chitin (aquaculture), algae slimes (algal culture) and biofouled surfaces may be quite advantageous.

It has been found that Microbulbifer expresses cell surface protuberances on its outer membrane and that they are expressed coincidentally with insoluble biopolymer degradation. Furthermore, results suggest that insoluble carbohydrate degradation is indeed most efficient in Microbulbifer when the carbohydrase systems are introduced and degradosome structures are expressed on the outer membrane of this Gram negative rod. Microbulbifer has been shown to a) synthesize greater quantities, and a greater variety, of degradable carbohydrase systems when grown in media containing several complex carbohydrate carbon sources than when grown in a single complex carbohydrate minimal media, b) package agarases and chitinases in different degradosome structures from one another, and c) undergo morphogenesis and synthesize interesting tubular structures under conditions of carbon limitation. In Microbulbifer a system of enzymes in the degradosome, acting in concert, degrade a portion of the carbohydrate to monomers, thus converting waste into usable nutrients. Living Microbulbifer may be used for bioremediation since it not a pathogen of animals or invertebrates.

Other genera shown to synthesize polysaccharide degrading enzymes (e.g. agarases) include Vibrio, Alteromonas, Flavobacterium, Streptomyces, and Pseudomonas. Microbulbifer produces three agarases with activities which are analogous to those of *P. atlantica*. However, the Microbulbifer agarases have different molecular weights, higher specific activity and are generally more resistant to denaturation than those of other species.

Alginate is commonly produced by both algae, such as *Macrocystis pyrifera*, and prokaryotes, such as *Azotobacter vinelandii*, and is consequently a major component of many biofilms. The alginic acid of mucoid *Pseudomonas aerugnosa* is of medical importance in the exacerbation of cystic fibrosis where it acts as a virulence factor, inhibiting host phagocytosis. Bacterial alginates differ from algal alginates in the degree of O-acetylation of the mannuronic acid residues. Chronic pulmonary infection with *Pseudomonas aeruginosa* is a major cause of mortality in cystic fibrosis patients. *Pseudomonas aeruginosa* produces a number of virulence factors including extracellular toxins, proteases, hemolysins and exopolysaccharides. The exopolysaccharide alginate shields the bacterium from the host defense mechanisms and anti-microbial agents. The exopolysaccharides may also promote adherence of mucoid strains to the epithelial cells of the respiratory tract. The use of an alginate lyase obtained from Flavobacterium OTC-6 as a therapeutic medicine for cystic fibrosis is described in U.S. Pat. No. 5,582,825. The alginate enzyme system produced by Microbulbiferdiffers from alginases purified from other organisms in that Microbulbifer produces an enzyme system made up of several enzymes which act together to more effectively degrade polysaccharides.

*Pseudomonas aeruginosa* infections also occur in burn victims, individuals with cancer and patients requiring extensive stays in intensive care units. Therefore, these patients would also benefit from an improved method for treating *Pseudomonas aeruginosa* infections.

In addition, many strains of *Streptococcus mutans* have been shown to be cariogenic in experimental animals and are directly associated with human dental caries (Hardie, J, M., 1981. The microbiology of dental caries. In: Silverstone, Johson, Hardie and Williams (ed.), Dental Caries: Aetiology, Pathology, and Prevention, The Macmillian Press Ltd, London, pp 48–69.; Tanzer, J. M. (ed), 1981, Animal Models in Cariology, Special Supplement, Microbiology Abstracts, Information Retrieval, Washington D. C. and London.) and can be isolated from cases of infective endocarditis. The primary habitat of *S. mutans* is the tooth surface of humans, and its colonization of this surface is favored by high levels of dietary sucrose. *S. mutans* produces biofilms which are composed of several types of extracellular polysaccharides which are manufactured from sucrose and which are important in the colonization of hard tissue surfaces in the mouth (Gibbons, R. J. and J. van Houte, 1973. On the formation of dental plaques. J. Periodontal. 44–347–360.; Gibbons, R. J. and J. van Houte, 1975. Bacterial adherence in oral microbial ecology. Ann. Rev. Microbiol. 29:1944.; Hamada, S. and H. D. Slade, 1980. Mechanisms of adherence of *Streptococcus mutans* to smooth surfaces in vitro. In: Beachey (ed.), Bacterial Adherence, Chapman and Hall, London, pp. 105–135.) These glucans include a water soluble $\alpha(1-6)$—linked linear glucose polymer with $\alpha(1-3)$ glucosidic branch linkages (Long, L. and J. Edwards,1972. Detailed structure of a dextran from a cariogenic bacterium. Carbohydr. Res. 24:216–217.), and other essentially water-insoluble, cell-associated polymers. These water-insoluble polymers contain a high proportion of $\alpha(1-3)$ glucosidic linkages and are generally resistant to degradation by enzymes commonly present in the oral cavity. Because these *S. mutans* produced biofilms are resistant to enzymatic degradation they build up on the tooth surface, are a major component of dental plaque, and provide an additional habitat for dental cary causing microbes and microbes which contribute to "bad breath." Currently, dental plaque is removed by physical scraping of the tooth surface which is most often performed by dental technicians. The *S. mutans* biofilm is only partially removed from the tooth surface by brushing with a dentifrice or by mouthwash. Consequently, an enzymatic preparation able to degrade the *S. mutans* produced polysaccharide biofilm and aid in the removal of dental plaque could be incorporated into a toothpaste, into a mouth rinse, or into other vehicles which contact the tooth surface. Enzymatically degraded *S. mutans* biofilm and the biofilm-associated microorganisms can be more easily and readily removed from the oral cavity resulting in fewer dental caries and objectionable mouth odors.

In view of the above discussion, one object of the present invention is to develop nontoxic, environmentally friendly methods for removing industrial biofilms.

Another object of the present invention is to develop a method for removing various disease related biofilms on an internal or external surface of an animal or on an implant prior to or after implantation in an animal by applying to the affected surface or administering to the animal an effective amount of a) an organism which produces a hydrolytic enzyme mixture, b) a hydrolytic enzyme mixture and/or c) a component of a hydrolytic enzyme mixture.

SUMMARY OF THE INVENTION

In the present invention, multiple specificity, hydrolytic enzyme mixtures are produced using certain bacterial species (e.g. marine saprophytic bacteria such as Microbulbifer 2–40 also known as Alteromonas 2–40). The bacteria are selected for their ability to grow on and catabolize or degrade a wide range of complex polysaccharide sources such as those that are present in biofilms. The bacteria are cultured in the presence of one or more polysaccharides which are present in the targeted biofilm. The polysaccharides are used as the primary carbon source to support the growth and metabolism of the bacteria. During the growth of the bacteria in the presence of the polysaccharide, a mixture of hydrolytic enzymes with multiple specificities capable of degrading a complex biofilm material containing the polysaccharide is produced. By altering the composition of the polysaccharides in the culture medium, a custom tailored mixture of enzymes can be produced. The hydrolytic enzyme mixture can then be isolated and applied to the affected industrial or biological surface.

The industrial application of a multiple specificity, hydrolytic enzyme mixture will remove or degrade biofilms from the target industrial surface causing a reduction of the biofilm thereby resulting in increased efficiency and improved hygiene.

The therapeutic administration of a hydrolytic enzyme mixture or a component thereof will reduce the biofilm and thereby enable antibiotics and/or the animal recipient's immune system to fight an infection with a bacterial pathogen. The therapeutic, multiple specificity, hydrolytic enzyme mixture of the present invention will therefore be useful as an adjunct to standard anti-infective therapies when a biofilm producing pathogen is involved.

When used therapeutically, the hydrolytic enzyme mixture of the present invention can be administered by any route, including but not limited to oral, pulmonary (by aerosol or by other respiratory device for respiratory tract infections), nasal, IV, IP and intra-ocularly.

Batch culture growth (Abs 600 nm)(-●-) and cell number (cfu/ ml)(-■-) were plotted vs time. Inset graph shows the relationship between OD(600 nm)(y-axis) and cell number (cfu/ ml)(x-axis) in glucose MM vs a glucose MM blank (-●-). Solid black line on inset graph is the linear regression.

Figure 3:
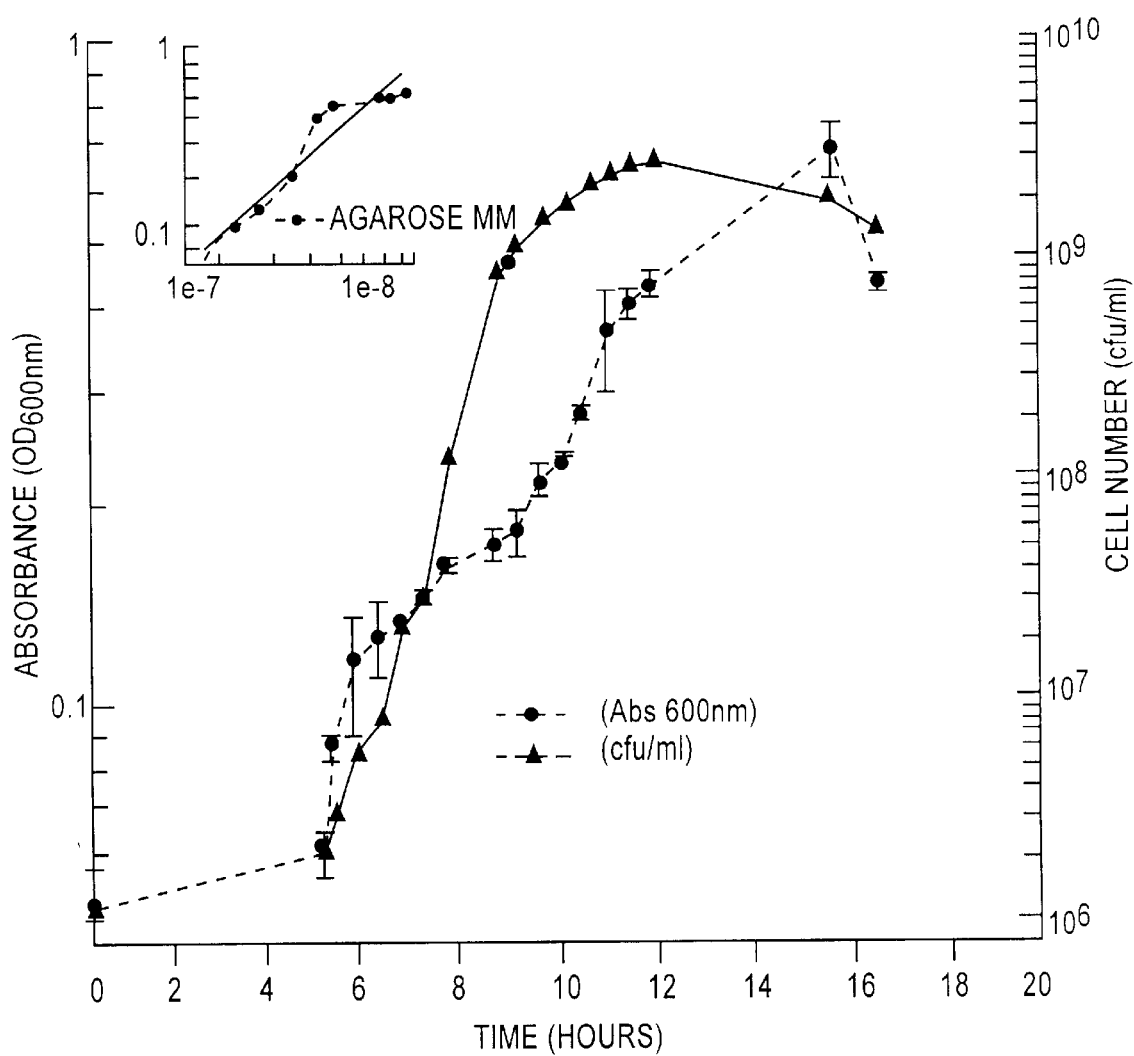

FIG. 3. Batch growth in 0.2% agarose minimal medium. A.

Batch culture growth (Abs 600 nm) (-▲-) and cell number (cfu/ml) (-●-) were plotted vs time. Inset graph shows the relationship between OD (600 nm)(y-axis) and cell number (cfu/ ml)(x-axis) in agarose MM (-●-). Solid line on the inset graph is the linear regression.

Figure 4:
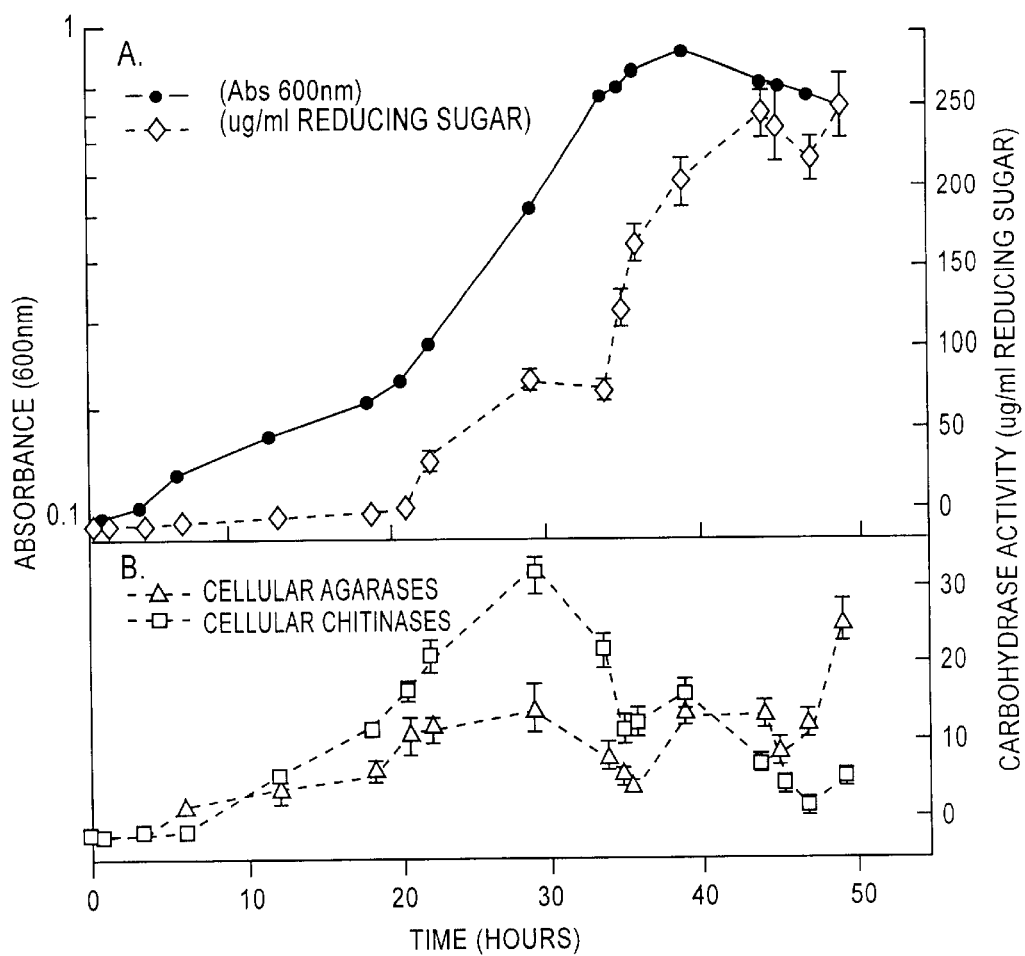

FIG. 4. Batch growth in 0.2% chitin minimal medium. A. Batch culture growth (Abs 600 nm)(-●-) and relative extracellular chitinase activity (-□-)(μg/ml reducing sugar) were plotted vs time. B. Relative carbohydrase activity (μg/ml reducing sugar) of cellular chitinases (-□-) and cellular agarases (-Δ-) produced by 2–40 grown in chitin MM (graphed in A.) were plotted vs time. There was no detectable extracellular agarase activity in 2–40 grown in chitin MM.

Figure 5A:
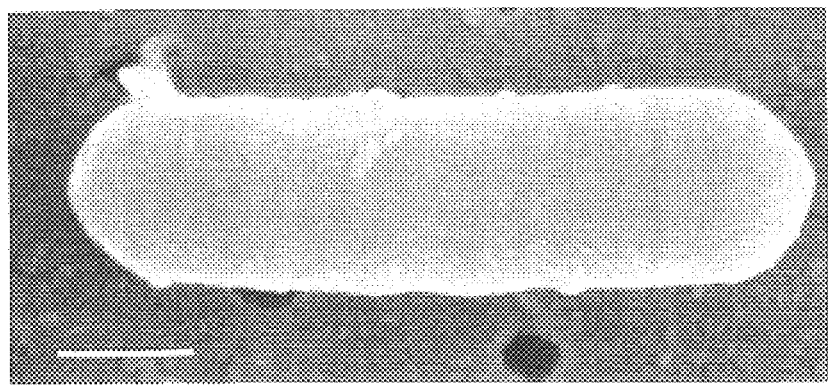
Figure 5B:
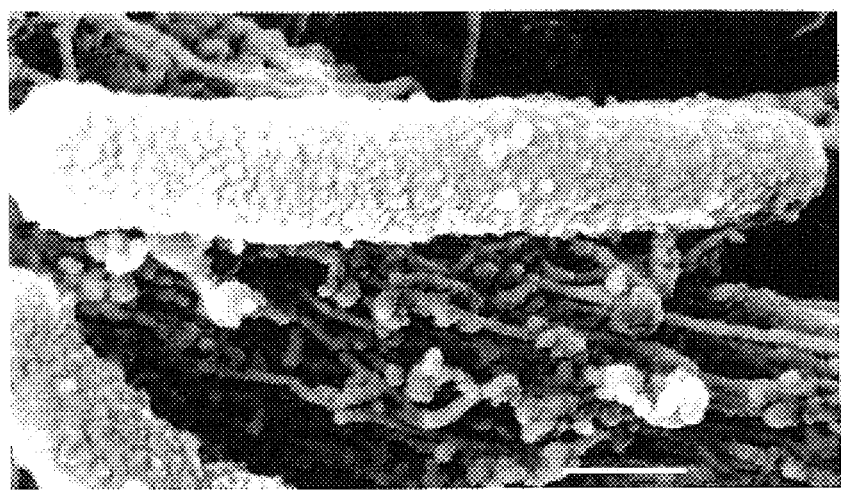
Figure 5C:
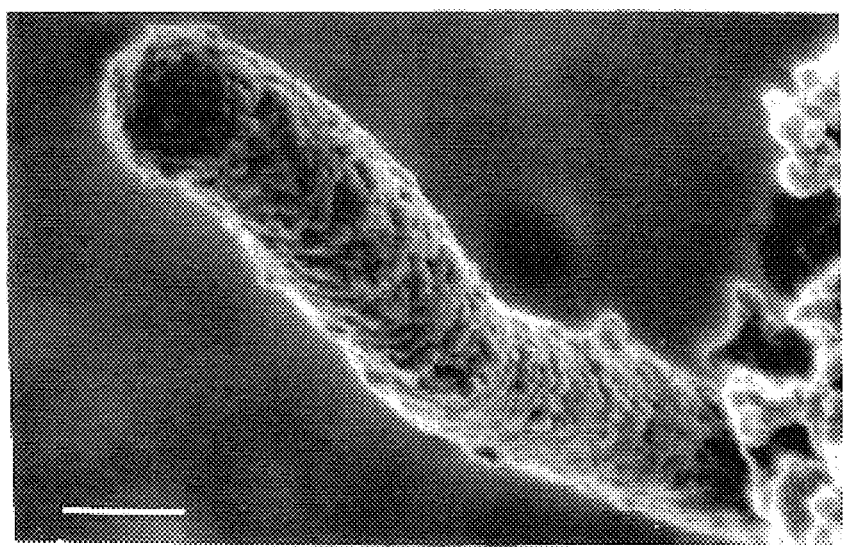

FIG. 5. Fine structure of 2–40 grown in 0.2% glucose (A), agarose (B), or chitin (C). Cells grown in the respective substrate to mid-log phase were observed by SEM. Note the rough surface (degradosome covered) of cells grown in ICP (B & C) and their absence in glucose (A). The production of these structures correlated to the respective, homologous ICP degradase activity. Scale bar=300 nm.

Figure 6:
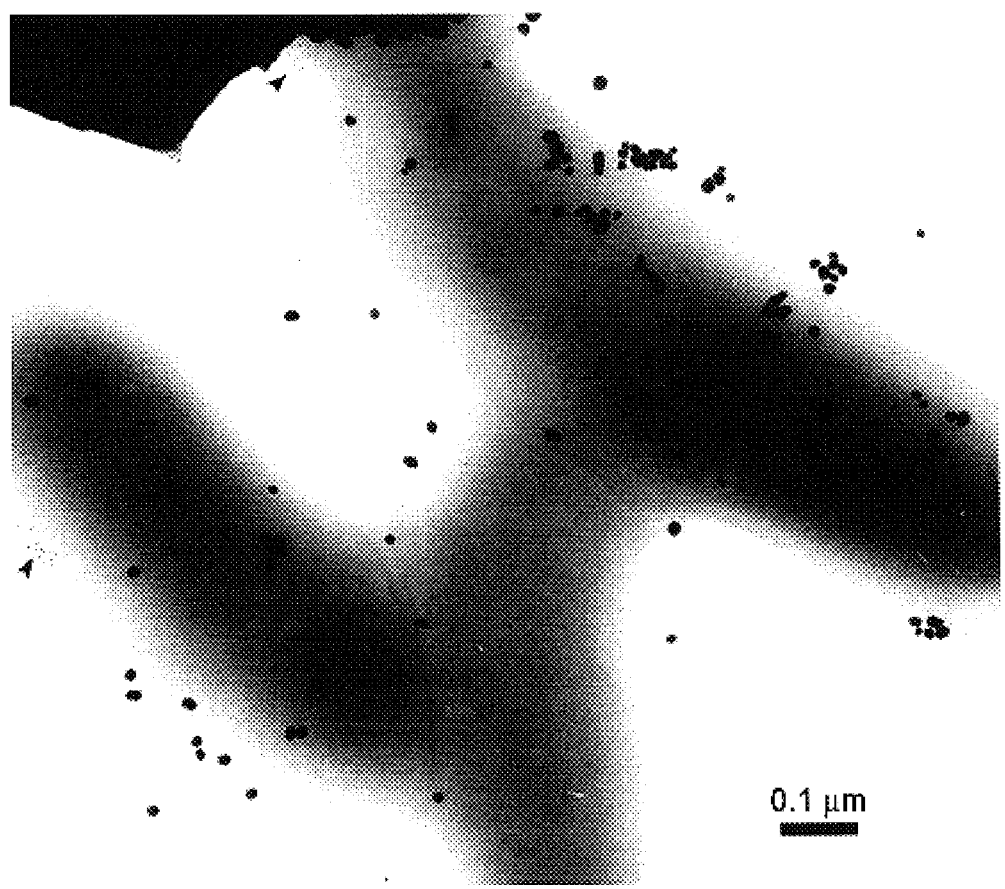

FIG. 6. Immunolabeling of agarase and chitinase synthesized simultaneously by 2–40. Whole cells of 2–40, grown to mid-log phase in MM containing 0.2% agarose and chitin, were labeled with anti-agarase antibody (primary) and 10 nm gold labeled goat anti-rabbit IgG antibody (secondary). They were additionally labeled with 20 nm gold labeled anti-chitinase antibody. Cells were stained with 1 % uranyl acetate and observed by TEM. Arrows indicate agarase labeling. Note the segregation of agarase (small gold particles) and chitinase (larger gold particles) labeling in the micrograph.

FIG. 7. Zymogram of 8% native-PA gel overlay with molecular weights added for reference. For both A and B Lane 1, 60 μg total protein of 0.2% glucose grown 2–40; Lane 2, 40 μg total protein of partially purified concentrated alginase preparations. Duplicate lanes of glucose 2–40 cell prep and alginase prep from the gel were (A) silver stained and (B) used in the zymogram overlay, then stained with toluidine blue O. There are eight bands with alginase activity with approximate molecular weight of 87, 66, 43, 39, 35, 27, 25 and 23 kD.

FIG. 8. Sequence from position 300 to 1500 of the 16S gene of Microbulbifer 2–40.

DETAILED DESCRIPTION OF THE INVENTION

The general methods and steps for preparing biofilm-degrading, multiple-specificity, hydrolytic enzyme mixtures are as follows. First, certain bacterial species (e.g. marine saprophytic bacteria as exemplified by Microbulbifer.) are selected for their ability to grow on and catabolize or degrade a wide range of complex polysaccharide sources including those that comprise biofilms. These selected bacterial species are then cultured in a medium or series of media containing one or more of the specific polysaccharides comprising the targeted biofilm, or derivatives thereof. The polysaccharides are used as the primary carbon source to support the growth and metabolism of the bacterial species. During growth of the bacterial species on this specialized medium, a mixture of hydrolytic enzymes with multiple specificities capable of degrading the complex biofilm material is produced on the surface of the organism in enzyme containing protuberances [for example through the formation of enzyme-containing appendages (degradosomes) from the bacterial cell surface] and elaborated from the cells in tubules or vesicles or otherwise released into the medium by the bacteria in increasing quantities as the insoluble complex polysaccharides are depleted, as exemplified by certain marine saprophytic bacteria such as Microbulbifer 2–40. By altering the composition of the polysaccharides or their derivatives in the culture media, a custom-tailored consortia of hydrolytic enzymes can be produced. The biofilm-degrading, multiple-specificity, hydrolytic enzyme mixtures are separated from the culture, preferably from the culture supernatant and more preferably from supernatant having hydrolytic enzyme-containing appendages or vesicles. The enriched hydrolytic enzyme mixture is appropriately formulated and applied to the biofilm which results in the degradation and removal of the biofilm targeted for the application. Alternatively, the living organism itself, the degradosorhes, tubules, vesicles or purified enzymes can be directly applied to the biofilm. It should be clear that since each biofilm forming microbial species produces a unique biofilm material, each biofilm will require a different, custom tailored, multiple-specificity, hydrolytic enzyme mixture to achieve biofilm control. These different mixtures can be produced and tailored for each use by employing the targeted biofilm material as the primary carbon source during the culture of the bacterial species. The enzyme mixture can then be purified and applied to the targeted biofilm.

The enzyme mixture can be purified as a mixture or the various enzyme systems present in the mixture can be purified individually. If the enzymes are purified individually an enzyme mixture can be reformulated after purification or the enzymes can be used individually (e.g. in some specific therapeutic applications). It is not necessary to completely purify the enzyme systems prior to use. The enzymes may be present in and purified from degradosomes, vesicles or tubules or the degradosomes, vesicles or tubules can be applied directly to the targeted biofilm.

In an industrial setting the amount of the enzyme mixture to be applied to the targeted biofilm is not critical. The amount to be applied can easily be determined by routine experimentation and will be related to the composition of the biofilm. In an industrial setting, the enzyme mixture is applied by contacting the targeted biofilm with the appropriate enzyme mixture.

In a therapeutic application, there is no particular limitation on the modality of treatment with the enzyme mixture of this invention and the composition can be administered according to a treatment protocol which depends on the patient's age, sex and other factors, the severity of disease, etc. A spray or an infusion can be directly applied to the affected site. A tablet, solution, emulsion, powder or capsule can be administered orally. An injection can be administered in admixture with an ordinary infusion fluid such as glucose solution, amino acid infusion, etc. Thus, the routes of administration include but are not limited to: oral, aerosol or other device for delivery to the lungs, nasal spray, intravenous, intramuscular, intraperitoneal, and topical. Excipients which can be used as a vehicle for the delivery of the enzyme mixture will be apparent to those skilled in the art. For example, the enzyme mixture could be in lyophilized form and be dissolved just prior to administration or the enzyme mixture could be present in liposomes. If the targeted biofilm is on an oral surface, the enzyme mixture could be applied in the form of a toothpaste or mouth rinse. The dosage of administration of the enzyme mixture for reducing biofilms on an oral surface is between 0.1 mg–1 g per ml of delivery excipient. The dosage of administration of the enzyme mixture for treating *P. aeruginosa* infections is contemplated to be in the range of about 0.1–1100 mg/per kg body weight, and preferably about 1–10 mg/per kg body weight.

With respect to the aerosol administration to the lungs, the hydrolytic enzyme mixture is incorporated into an aerosol formulation specifically designed for administration to the lungs by inhalation. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane and oleic acid. The concentrations of the propellant ingredients and emulsifiers are adjusted if necessary based on the enzyme mixture being used in the treatment. The enzyme mixture can also be administered using a nebulizer. When aerosol administration to the lungs is used, a bronchodilator such as aminophylline, an antibiotic drug such as a β-lactam (e.g. penicillin, cephalosporin) or quinolone, a DNase, a protease inhibitor and/or an amiloride, can be combined with the enzyme mixture for enhanced therapeutic efficacy.

The enzyme mixture can be administered in combination with antibiotics or other antimicrobial substances, other therapeutic proteins and/or mild abrasives. Suitable antibiotics include but are not limited to tobramycin and duramycin. Other suitable antibiotics will be apparent to those in the art once the organism producing the biofilm is determined. Therapeutic proteins useful in combination with the enzyme mixtures of the present invention include but are not limited to Dnases.

The foregoing embodiments of the present invention are further described in the following Examples. However, the present invention is not limited by the Examples, and variations will be apparent to those skilled in the art without departing from the scope of the present invention.

EXAMPLES

Example 1
Effect of Sole Carbon Sources on the Production of Carbohydrases

Media, chemicals and growth parameters. To assess the production of carbohydrases when using various carbon sources, 2–40 was grown in minimal media (Table 1) containing a final concentration of 0.2% of one of the following carbon sources: agar or its degradation products (neoagarotetraose, neoagarobiose, D-galactose), alginic acid, carrageenan, carboxymethyl cellulose, colloidal chitin or its degradation products (chitobiose, chitotriose, N-acetyl-D-glucosamine), D-glucose (previously reported to repress the Microbulbifer 2–40 agarase system and other bacterial chitinase systems) (Stosz, 1994; Frändberg & Schnürer, 1994), laminarin (determined to repress chitinase systems in other bacteria) (Frändberg & Schnürer, 1994), β-glucan (determined to repress other bacterial chitinase systems) (Frändberg & Schnürer, 1994), pectin (determined to induce other bacterial chitinase systems) (Frändberg & Schnürer, 1994), pullulan, starch (selected based on previous finding that it repressed other bacterial chitinase systems) (Frändberg & Schnürer, 1994), xylose, or xylan. All complex carbohydrates were added to the medium prior to autoclaving. All oligo- and mono- saccharides were prepared as 20% stocks in Pipes buffer, filter sterilized and added to cooled media (cooled to 45° C.). The cultures were grown at room temperature with constant aeration, shaking at 200 rpm. During bacterial growth, the $OD_{600nm}$ was determined, compared with a standard viable growth curve to obtain cell counts, and growth curves were generated. All chemicals were purchased from Sigma Chemical Co. (St. Louis, Mo.), except for chitobiose and chitotriose (Seikagaku, Rockville, Md.) and agarose (FMC, Rockland, Me.).

TABLE 1

Media.

| Name | Composition |
|---|---|
| MM (minimal medium) | 23 g/L sea salts |
| | 1.0 g/L yeast extract |
| | 2.0 g/L polysaccharide[a] |
| | 50 ml/L Tris-HCL, pH 7.6 |
| | 0.5 g/L NH$_4$Cl |
| LM (Luria Marine)[b] | 10 g/L bacto-tryptone |
| | 5 g/L yeast extract |
| | 20 g/L NaCl |
| | 0.1 g/L chitin |
| | adjust pH to 7.5 |
| MM agar plates | MM + 1.5% agar |
| Chitin MM plates | 23 g/L sea salts |
| | 1.0 g/L yeast extract |
| | 2.0 g/L chitin paste[c] |
| | 20 g/L phytagel |
| MA plates (Marine agar) | 37.4 g/L Marine broth |
| | 1.5 g/L agar |

[a]Insoluble polysaccharides were added to media prior to autoclaving. Other carbon sources were filter sterilized in 20 mM Pipes buffer, pH 6.8 and added to cooled media to produce a final concentration of 0.2%.
[b]*Vibrio harveyi* BB7-1 was cultured in this medium
[c]chitin paste was produced as outlined by Lingappa and Lockwood (1962).

TABLE 2

Reagents.

| Reagent | Composition |
|---|---|
| Silver Stain Fixing Solution | EtOH: glacial acetic acid: H$_2$O |
| | 30:10:60 |
| Silver Stain Developer | 2.5% sodium carbonate |
| | 0.02% formaldehyde |
| Coomassie Blue Stain | 0.125% Coomassie Blue R-250 |
| | 50% Methanol |
| | 10% glacial acetic acid |
| Coomassie Blue Destain Solution I | 50% methanol |
| | 10% acetic acid |
| Coomassie Blue Destain Solution II | 7% acetic acid |
| | 5% methanol |
| Imidazole-Zinc Equilibration Solution | 0.2M Imidazole |
| Imidazole-Zinc Staining Solution | 0.3M ZnSO$_4$ |
| Imidazole-Zinc Destaining Solution | 2% citric acid |
| India Ink Stain | 0.3% Tween 20/PBS |
| | 0.1% India Ink |

TABLE 2-continued

Reagents.

| Reagent | Composition |
| --- | --- |
| LPS Stain Fixing Solution | 40% EtOH |
| | 5% glacial acetic acid |
| Periodic Acid Oxidizing Solution | 0.833% periodic acid |
| LPS Stain Solution | 0.075% NaOH |
| | 0.8% silver nitrate |
| | 1.4% (v/v) ammonium hydroxide |
| LPS Stain Developing Solution | 50 mg/L citric acid |
| | 190 µl/L formaldehyde |
| Iodine Stain | 0.1M KI |
| | 0.05M I |
| Triton Solution buffer, | 2.5% Triton X-100 in 20 mM Pipes pH 6.8 |
| Dinitrosalicyclic acid Reagent (DNSA) | 2.14% NaOH |
| | 0.63% 3,5-dinitrosalicyclic acid |
| | 0.5% phenol |

TABLE 3

Buffers.

| Buffer | Composition |
| --- | --- |
| Pipes Buffer | 20 mM Pipes buffer, pH 6.8 |
| PBS Buffer | 8 g/L NaCl |
| | 0.2 g/L KCl |
| | 1.44 g/L Na$_2$HPO$_4$ |
| | 0.24 g/L KH$_2$PO$_4$ |
| | adjust pH to 7.4 with HCl |
| Immunoblotting Buffer | 2.93 g/L glycine |
| | 5.81 g/L Tris |
| | 0.375 g/L SDS |
| | 20% (v/v) methanol |
| Sodium Acetate Buffer | 14.8 ml of 0.2M acetic acid |
| | 35.2 ml of 0.2M sodium acetate |
| | 50 ml of dH$_2$O |
| | pH 5.0 |
| Western Development Buffer I | 80 mM Tris-HCl, pH 8.0 |
| | 0.4 mg/ml 4-chloro-1-napthol |
| | 0.1 µg/ml H$_2$O$_2$ |
| | (for HRP labeled antibody detection) |
| Western Development Buffer II | 0.15 mg/ml 5-bromo-4-chloro-3-indolylphosphate |
| | 0.3 mg/ml nitro blue tetrazolium |
| | 100 mM Tris buffer |
| | 5 mM MgCl$_2$ |
| | (for AP labeled antibody detection) |
| ELISA Development Buffer | 24.3 mM citric acid, pH 5.0 |
| | 51.4 mM NaH$_2$PO$_4$ |
| | 0.04% o-phenylenediamine |
| | 0.04% H$_2$O$_2$ |
| Carbonate Buffer | 10.6 g/L Na$_2$CO$_3$ |
| | adjust to pH 9.6 |
| Acetate Buffer | 126.5 ml of 0.2M acetic acid |
| | 373.5 ml of 0.2M sodium acetate |
| | 500 ml dH$_2$O |
| | Adjust pH to 5.1 |
| Embedding fixation buffer | 3.5% NaCl |
| | 3% formaldehyde |
| | 0.1% gluteraldehyde |
| | in 20 mM phosphate buffer, pH 7.0 |
| Native PAGE Treatment buffer | 12.5 mM Tris, pH 6.8 |
| | 10% glycerol |
| | 0.05% bromophenol blue |
| SDS-PAGE Treatment buffer | Native PAGE treatment buffer with 2% sodium dodecyl sulfate (SDS) |

Viable plate counts. For each time point viable plate counts and optical density (OD$_{600}$) were made in triplicate. The culture was vortexed thoroughly, to disrupt aggregated or substrate-bound cells, and plated on MM containing the sole carbon source. Plates, depending on the type of is MM, were incubated for 24 to 48 hours.

Enzyme harvesting. Carbohydrase activity was determined in crude enzyme preparations. These preparations consisted of whole cells or supernatant. At each time point, 100 ml of culture was centrifuged (10,000×g, 15 min., 4° C.) and the supernatant and cell pellet were separated. The supernatant was stored at −20° C. until used. The whole cells were washed twice in 50 ml of Pipes buffer and then resuspended in 2ml of buffer. The concentrated whole cells were also stored at −20° C. until enzyme activity was assayed.

Dinitrosalicyclic acid (DNSA) reducing sugar assay. The DNSA assay uses dinitrosalicyclic acid reagent, developed by Sumner and coworkers (Sumner & Sisler, 1944), to quantitate the amount of carbohydrase activity (µg/ml) by measuring the resulting reducing sugars present in the sample. In general, the 3,5-dinitrosalicyclic acid is reduced to 3-amino-5-nitrosalicyclic acid and the aldehyde groups are oxidized to carboxyl groups (Hostettler et al., 1951). Color change in DNSA reagent is detected spectrophotometrically as it becomes reduced by any reducing sugar present in a reaction mixture.

The enzyme preparation (spent media, whole cells, or concentrated enzyme preparations) (0.3 ml) was incubated with 0.7 ml of substrate (the various carbohydrates listed above). Substrates were prepared as 0.5% stocks except for agarose, which was 0.2%, in buffer of either pH 5.0 (0.025 M sodium citrate buffer) or pH 7.0 (0.01 M potassium phosphate buffer) depending on the polysaccharide. Carboxymethyl cellulose (Pettersson & Porath, 1966), chitin (Jeuniaux, 1966), laminarin (Ruse & Mandels, 1966) and pectin (Albersheim, 1966) were prepared in pH 5.0 buffer. Agarose, alginic acid (Preiss, 1966), carrageenan, pectin, pullulan, starch, and xylan were prepared in buffer of pH 7.0. Agarose alginic acid, chitin and carrageenan were boiled for 5 min. to dissolve them in the respective buffer prior to their addition to the reaction mixture. The reaction incubation time and temperature were also dependent upon substrate. Agarase, alginase, and xylanse activity reactions were incubated for 1 hour at 25° C., while cellulase, chitinase, carrageenase, laminarinase, pectinase, pullulanase and amylase reactions were incubated for 2 days at 30° C.

Following incubation, 1 ml of DNSA reagent (2.14% NaOH, 0.63% 3,5-dinitrosalicyclic acid, 0.5% phenol) was added to the reaction mixture and the samples were boiled for 5 min. in a hot water bath. Samples were cooled to room temperature and the absorbance at 575 nm was determined. The spectrophotometer was blanked against reaction mixtures with buffer replacing the enzyme preparation. Negative controls contained heat inactivated enzyme preparations, autoclaved prior to the addition to the reaction mixture. The amount of reducing sugar generated was determined by comparison to a galactose standard curve (20–600 µg galactose or reducing sugar equivalents) following any necessary adjustment for residual reducing sugar present in any negative controls. A standard curve was generated for each new batch of DNSA reagent prepared. DNSA assay values are recorded as µg of reducing sugar equivalents generated per ml of sample. Triplicate samples were prepared for each reaction and their average was taken to determine the µg/ml reducing sugar produced.

Carbohydrase activity in sole carbon sources. To assess the regulation of the carbohydrases by sole growth substrate, 2–40 was grown in minimal medium containing a final concentration of 0.2% of one of 16 sole carbon sources. Monosaccharides included: glucose, D-galactose, glucosamine, N-acetyl-D-glucosamine (NAG), and xylose. Insoluble complex polysaccharides included: agarose, alginic acid, carrageenan, carboxymethyl cellulose (CMC), chitin, glucan, laminarin, pectin, pullulan, starch, and xylan. Batch culture growth ($OD_{600nm}$) was monitored (FIGS. 1, 2, 3 & 4) and carbohydrase activity was assayed in both cellular and supernatant culture fractions (Tables 4 & 5).

Enzymatic activity was reported either as total relative μg/ml of carbohydrase activity to report 2–40 carbohydrase activity, or as units (μg/ml carbohydrase activity per μg/ml total sample protein per DNSA assay reaction time.

Example 2
Production and Purification of Enzyme Systems

Chemicals, media and bacterial growth conditions. Pseudomonas atlantica agarase (Sigma Chemical Co., St. Louis, Mo.) and chitinase, harvested from Vibrio harveyi, served as positive controls in zymograms. Broth media was prepared as described in Example 1 (Table 1). Cultures were also grown on solid media. Solid agar plates were made by adding 1% agar to the MM broth recipe (Table 1).

To induce chitinase production without agarase production, 2–40 was cultured on MM plates containing a purified chitin paste and were hardened with phytagel (Table 2.1). Chitin paste was purified from commercial chitin as outlined by Liggappa and Lockwood (1962). Practical grade chitin was soaked in 1 M NaOH for 24 hours After the chitin was washed with $dH_2O$, it was soaked in 1 M HCl for 24 hours, washed again with $dH_2O$, and transferred to 1 M NaOH. The alternate base/ acid soaking step was repeated four times as described. Following the final washing, the chitin was washed 4 times with 95% EtOH and dissolved in 2 vol. of 12 N HCl, with constant stirring for 20 min. at room temperature. After filtering the solution through glass wool into an equal volume of ice cold $dH_2O$ with constant stirring, the mixture was sedimented overnight. The sediment was washed 4 times with $dH_2O$ and the pH adjusted to 7.0 with 10 M NaOH. Following centrifugation (10 min. at 4,000 rpm), the chitin paste was stored in $dH_2O$ at 4° C. until used.

Agarase purification by ultrafiltration and ammonium sulfate precipitation. The β-agarase I and chitinase were purified and polyclonal antibodies were raised against them to be utilized in immunoelectron microscopy. It was previously determined (Stosz, 1994), and confirmed in these studies, that maximal agarase was produced in stationary phase supernatant when the organism was grown in agarose MM. The stationary phase supernatant (28 hours of culture growth) from 4L of culture of Microbulbifer 2–40 grown in 0.2% agarose MM was harvested by centrifugation (10,000× g, 15 min., 4° C.). Supernatant protein was concentrated to approximately 100 ml using a Minitan Manostat tangential flow ultrafiltration system (Millipore, Piscataway, N.J.) equipped with 30,000 dalton molecular weight cut off tangential flow filters. A buffer exchange was performed by passing 1 L of Pipes buffer (Table 2.3) through the system until the initial volume of 100 ml was obtained. All subsequent steps were performed at 4° C. The ultrafiltrate was subjected to a 40% ammonium sulfate (AS) cut. This concentration of AS was previously determined to adequately precipitate the β-agarase I of interest (Stosz, 1994). Saturated AS (4.1 M) was added dropwise to the concentrated supernatant with constant stirring. The sample was incubated for 1 hour to allow for equilibration before centrifugation (16,000×g, 15 min.). The resulting protein pellet was resuspended in 10 ml of Pipes buffer. The crude agarase preparation was desalted by overnight dialysis against Pipes buffer. Following centrifugation (16,000×g, 15min.), the remaining insoluble pellet was discarded and the soluble crude agarase preparation was concentrated by centrifugation in a Centriprep-30 (30 kDa MW cut off; Amicon Inc., Beverly, Mass.). This concentrated sample is referred to as the crude agarase preparation or the 40% AS cut. Total protein concentration and enzyme activity were assayed, as in Example 1, with the BCA protein assay and the DNSA reducing sugar assay.

Figure 1A:
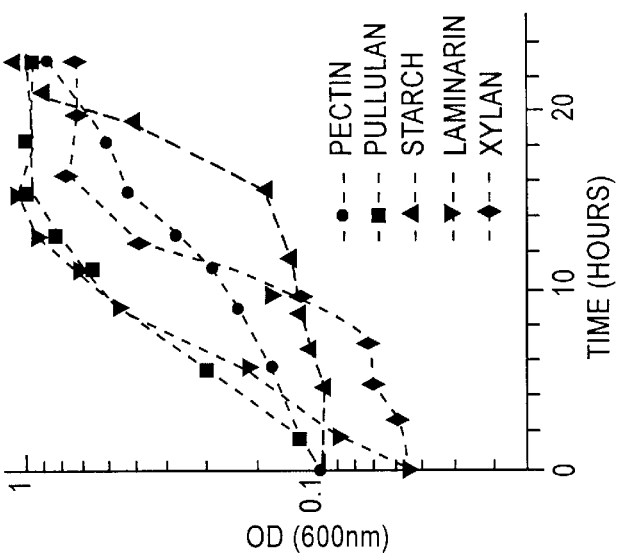
FIG. 1. Growth in monosaccharides or ICP as sole carbon sources. 2–40 was grown in MM+0.2% of the indicated sole carbon source. Batch culture growth ($OD_{600nm}$) was plotted vs. time: Growth in monosaccharides (A.) and Growth in ICP (B. & C.). Growth in other sole carbon sources is shown in subsequent figures: glucose, FIG. 2; agarose, FIG. 3; and chitin, FIG. 4. The cultures were sampled in time course for enzyme activity (see Table 4).
Figure 1B:
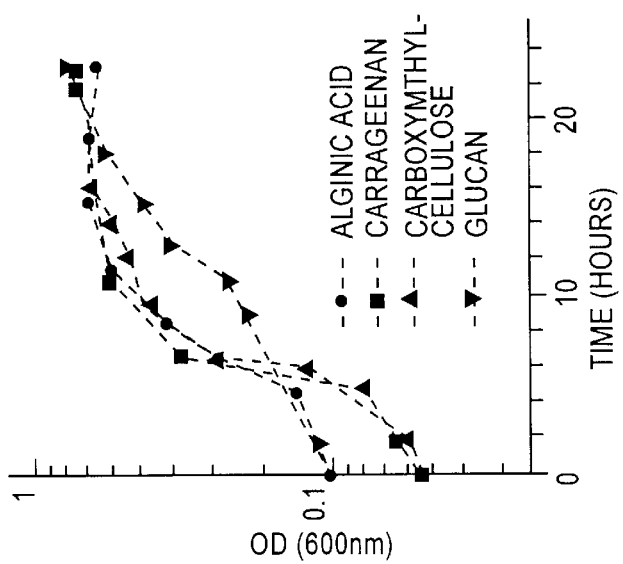
Figure 1C:
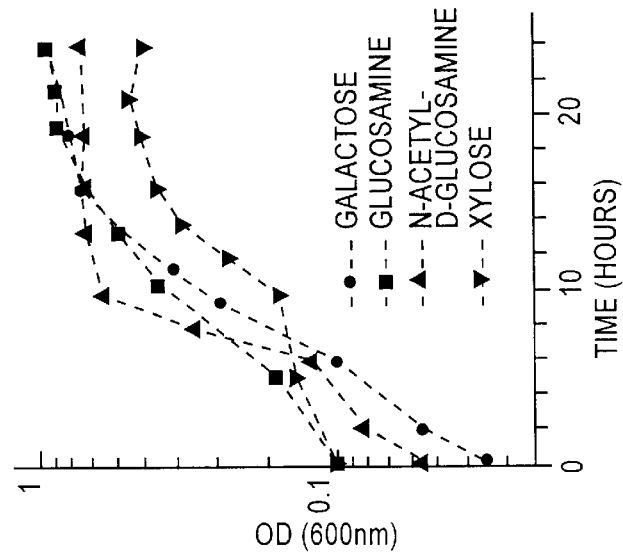
Figure 2:
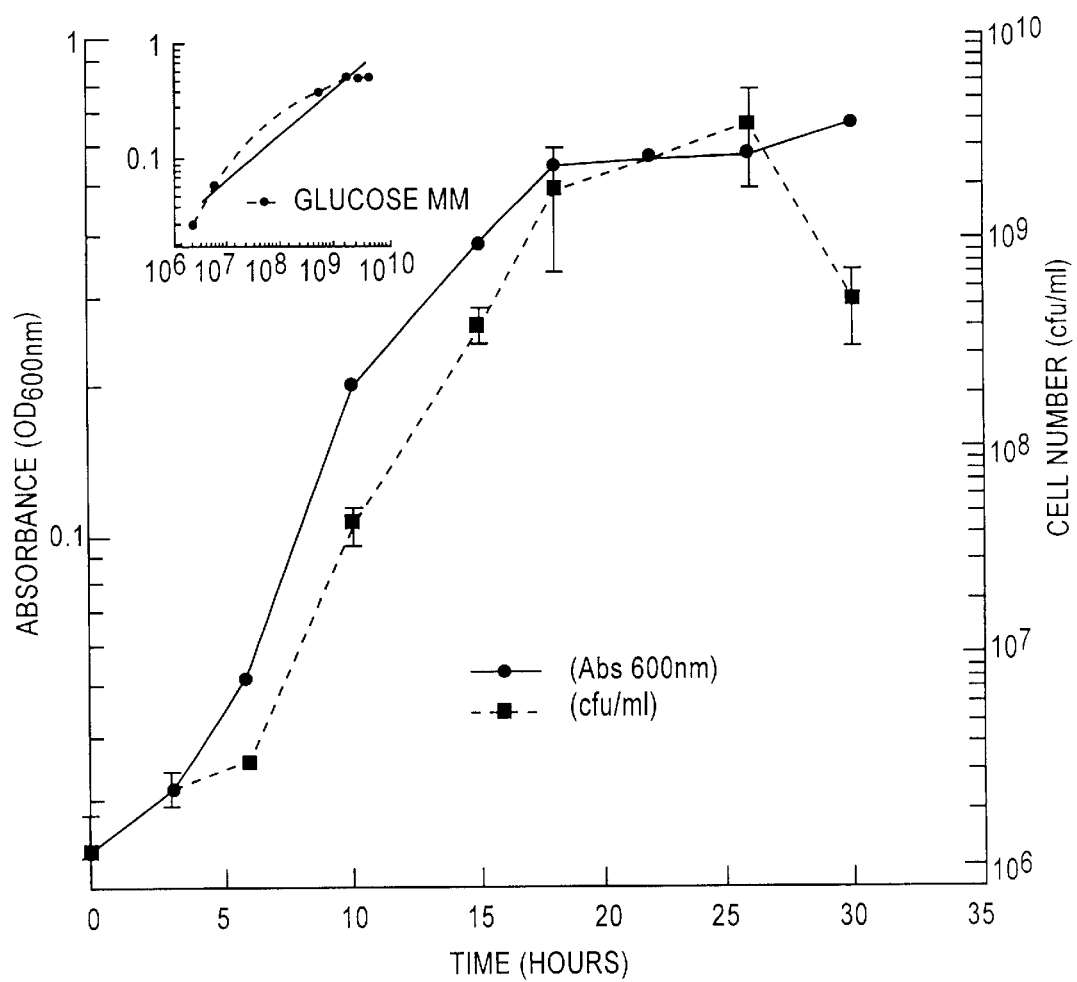
FIG. 2. Batch growth in 0.2% glucose minimal medium. A.

Chitinase purification. It was determined that early stationary phase supernatant contained the bulk of chitinase activity when Microbulbifer 2–40 was grown in MM supplemented with 0.2% colloidal chitin (FIG. 2.4). Four liters of early stationary phase culture supernatant (40 hours) were harvested by centrifugation and concentrated with the Minitan systems described above. One liter of 10 mM Tris buffer, pH7.3 was used to perform a buffer exchange in the Minitan system. The resulting 100 ml of crude chitinase preparation was further concentrated in Centriprep-30s. The resulting 15 ml was referred to the crude chitinase preparation and was stored at −70° C. until used. Total protein concentration and enzyme activity was determined for the crude enzyme preparation.

Vibrio harveyi chitinase harvest. V. harveyi BB7-1 was obtained and chitinase produced by it was harvested to use as a control in developing chitiriase enzyme assays and zymograms. The bacterium was grown in 1 L of LM supplemented with chitin (Table 1), to induce the clone's overproduction of chitinase, at 25 ° C. with shaking (100 rpm) for 3 days.

The sample was centrifuged (10,000×g, 15 min., 4° C.) and the supernatant collected. The extracellular chitinase was concentrated in Centriprep-10s and a buffer exchange was performed with 10 mM Tris, pH 7.3. The crude chitinase preparation was stored at −70° C. until used.

Polyacrylamide gel electrophoresis of crude enzyme preparations.

The crude enzyme preparations were analyzed on a discontinuous SDS- or native-PAGE as described by Laemmli (1970) using non-denaturing conditions (excluding boiling of the sample prior to electrophoresis and the addition of β-mercaptoethanol to the 2×PAGE treatment buffer), unless otherwise indicated. Non-denaturing conditions allowed for the enzymatic activity of separated protein bands to be determined directly in the separating gel or an overlay gel following electrophoresis. Gels used as agarase zymograms, to detect agarase activity, had 0.1% agarose incorporated in the separating gel. To detect chitinase activity, 0.05% glycol chitin, prepared as described below, was included in a duplicate overlay gel. Protein samples were diluted in the appropriate 2×PAGE treatment buffer (Table 3), either native- or SDS-, and allowed to incubate for 20 min. prior to gel loading of the samples. SDS-PAGE molecular weight standards were included on SDS-PAGES to allow for calculation of separated protein molecular weights (Bio-Rad, Richmond, Calif.). Following separation of the proteins by electrophoresis, the separating gel was stained by one of the following methods or processed as a zymogram.

Zymograms (activity gels). To detect proteins possessing β-agarase activity in PAGE gels, 0.1 % agarose was incorporated into the separating gel. Following protein separation by electrophoresis, native PAGE gels were placed in 100 ml of Pipes buffer and washed while shaking at room temperature for 10 min. The buffer was drained and replaced once. The gel was incubated overnight at 45° C. To visually identify agarases, the gel was stained with iodine solution (Table 2) for 10 min. at 25° C. while shaking. Enzymatic protein bands appeared clear on a brown background. SDS-PAGE zymograms were treated as described, following two 20 min. initial washings of the gel in 100 ml of 2.5% Trition X-100 in Pipes buffer to remove SDS, rendering the enzymes active. The iodine stains only solidified agarose, not any oligosaccharide degradation products, resulting from agarase activity (Ng Yin Kin, 1972). Only β-agarases (I & II), degrading polysaccharide to oligosaccharide, were semi-quantitatively stained.

Glycol chitin was produced by acetylation of glycol chitosan (Sigma Chemical Co., St. Louis, Mo.), as outlined by Trundel and Asselin (1989), and used in PAGE detection of chitinases. All procedures were performed at room temperature unless indicated. Glycol chitosan (10 g) was dissolved in 200 ml of 10% acetic acid by grinding the mixture in a mortar. After the solution stood overnight, 900 ml of methanol were added slowly and the resulting solution was vacuum filtered through Whatman No. 4 paper. To the filtrate, 15 ml of acetic anhydride was added while stirring. A gel was produced and allowed to stand for 30 min., before cutting it into small fragments. Any liquid resulting from the gel fragmentation was discarded. A Waring blender (4 min. at max. speed) was used to homogenize the gel pieces which were covered with methanol. The mixture was centrifuged (27,000×g, 15 min., 4° C.) and the pellet was resuspended in 1 vol. of methanol, rehomogenized and centrifuged as described. The final glycol chitin pellet was resuspended in 1 L of $dH_2O$+0.02% $NaN_3$ and homogenized. The resulting 1% (w/v) glycol chitin stock was stored at 4° C. until used.

Chitinase zymograms, containing 0.05% glycol chitin in the separating gel, were developed as described by Pan et al. (1991). Following electrophoresis, the native-PAGE was incubated for 5 min. In 150 mM sodium acetate buffer, pH 5.0. The buffer was replaced with fresh buffer and the gel was incubated for 2 hrs. at 37° C. After the buffer was removed, the gel was stained with 0.01% (w/v) Calcoflour White M2R in 500 mM Tris-HCl, pH 8.9 for 5 min. at room temperature. Calcoflour is light sensitive, so the gel was covered for staining and the remaining steps. The stain was removed and the gel destained overnight in $dH_2O$ at room temperature. Chitinase bands were detected by observation of the gel on a transilluminator and photographic documentation was made with a thermal printer.

Silver staining of proteins. Silver staining of electrophoretically separated proteins allows for the most sensitive detection of them, detecting as little as 0.1–1.0 ng of protein in a single band, and is approximately 100- to 1000-times more sensitive than Coomassie Blue staining. The silver ions, following staining with silver nitrate, are bound to the side chains of the proteins amino acids and are differentially reduced upon development (Merril et al., 1984). Free amines and sulfur groups are the principal reactive groups of the protein (Freeman, 1973; Heukeshoven & Dernick, 1985; Neilsen & Brown, 1984).

Silver staining was performed as outlined by Sambrook et al. (1989), a modification of the original staining procedure described by Sammons et al. (1981). All procedures were performed at 25° C., the gel was gently shaken during incubation periods, and HPLC grade water was used. Proteins were fixed in the gel following separation by electrophoresis by overnight incubation in 300 ml silver stain fixing solution (Table 2). The fixing solution was discarded and the gel incubated for 30 min. in 30% EtOH. The gel was washed with 4 changes of HPLC water, for 10 min. each, and stained with 0.1% $AgNO_3$ for 30 min. The $AgNO_3$ solution was then discarded and the gel was washed under a stream of HPLC water for 40 sec. The protein bands were developed by 300 ml of silver stain developing solution (Table 2) for 10–30 min., until the desired visual development of the bands was achieved. Development was ceased by incubation of the gel for 10 min. in 1% acetic acid. All gels were washed and stored at 4° C. in $dH_2O$.

Coomassie blue protein staining. The Coomassie Blue R-250 protein stain described by Diezel et al. (1972) was used to detect predominant proteins in preparative gel when purity and trace protein detection was not of significant importance. Coomassie blue stain (Table 2) was heated to 45° C. and incubated with the gel at 25° C. for 2 hours with gentle shaking. After discarding the staining solution, the gel was destained with Coomassie blue destaining solution (Table 2) at 25° C. with constant shaking and several changes until protein bands were distinguishable in the gel. If stained gel sections were used to identify enzyme bands to be excised from a preparative gel, the gel fragments were shrunken (in methanol) or swollen (in $dH_2O$) until the gel fragments matched the size of the initial separating gel, just prior to excising of the protein band. The stained outer gel fragments were matched up with the mid-section of the separating gel to estimate the position of the enzymatic band to be excised from the gel. The excised get band was washed with PBS and crushed as described below. This staining method was only used for native PAGE, since imidazole-zinc staining is only compatible with SDS-PAGEs.

Imidazole-zinc protein staining. The imidazole-zinc protein stain allowed for visual detection of the protein band of interest on preparative SDS-PAGE. The protein could then be excised and destained. This method, described by Fernandez-Patron et al. (1992), allows for detection of proteins by negatively staining them and is only slightly less sensitive that silver staining. Following electrophoretic separation of the proteins, the SDS-PAGE was soaked in $dH_2O$ for 10 seconds. The gel was incubated in 200 ml of 0.2 M imidazole for 10 min. at 25° C. while gently shaking. The imidazole solution was removed and the gel was negatively stained for 2 min. in 200 ml of 0.3 M $ZnSO_4$ at room temperature while rocking. The protein band of interest, a clear band against an opaque background, was excised form the gel and destained for 10 min. in 2% citric acid. The gel fragment was washed with several changes of Pipes buffer+ 2.5% Triton X-100. The gel fragment, containing the enzyme of interest, was washed with PBS and finely sliced. The gel fragments were loaded into a syringe with PBS and crushed by passing the mixture back and forth between two glass syringes connected by an 18 gauge hub. This mixture of crushed acrylamide and PBS was frozen at −70° C. until use.

Topographical protuberances (Degradosomes). 2–40, grown in MM containing 0.2% agarose or chitin, attach to the insoluble substrate while growing on it. Additionally, both transmission and scanning electron microscopic examination of Microbulbifer 2–40 whole cells revealed novel cell surface structures that were elaborated coincidentally with the degradation of agarose (FIG. 5) and chitin (FIG. 6) and the induction of the respective degradative enzyme system. These structures were not synthesized by cells that were agarase and chitinase repressed by glucose. These structures are refered to generally, as degradosomes. There were several hundred degradosomes on the cell surface. They are typically 40–60 nm wide. They extend less from the cell surface during early growth phases and they extend further during late culture stages.

Immunolabeling of agarase and chitinase in degradosomes. To determine whether degradative enzymes were localized in degradosomes, whole cells and ultrathin sections of Microbulifer 2–40 grown under carbohydrase-inducing or -repressing conditions were immunolabeled with absorbed anti-agarase and/or -chitinase antisera. Agarases and chitinases were concentrated and localized in the degradosomes of cells cultivated in 0.2% agarose or chitin MM, respectively. These structures initially appear as cell surface blebs. In later growth stages they elongate into tubules or they form nodules. Eventually they are released into the culture supernatant. These structures were not present in mid-log phase cultures of glucose grown cells which also were not labeled with either anti-agarase or -chitinase antisera. Additionally, statistical analysis of immunolabeled thin sections provides strong evidence for the production of agarosomes and chitinosomes, as well the lack of degradosomes in controls. Control pre-immune serum did not label whole cells and thin sections grown in glucose, chitin or agarose MM.

Double labeling immunoelectron microscopy, using both anti-agarase and -chitinase to label the respective enzyme, was done to: 1) determine if both enzyme systems are induced in a single cell; 2) when both were produced; 3) see whether both enzyme systems were localized in the same degradosome. 2–40, grown in MM plus 0.2% agarose and chitin to mid-log phase, was labeled with anti-agarase antibody and anti-chitinase antibody. Both the agarase and chitinase systems were active in cells sampled during growth. The agarase was labeled with smaller colloidal gold particles, 10 nm, and chitinase with larger particles, 20–30nm. Double labeled whole cells and ultrathin sections showed that both enzyme systems were synthesized in a single cell and that each segregated into a different degradosome.

Extracellular agarase production. Microbulbifer 2–40 synthesizes a β-agarase system comprised of numerous extracellular agarases, with predominant agarases of 98, 90, 60, and 42 kDa. Many of these degradative agarases are packaged in tubules, vesicles or other elaborated structures. Other species, *P. atlantica*, Vibrio sp. strain JTO107, and a Pseudomonas like bacteria, synthesize multiple agarases, which arguably work cooperatively to degrade the substrate (Sugano et al., 1994; Bibb et al., 1987; Belas et al., 1988; Malmqvist, 1978). The multiple agarases of Microbulbifer 2–40 appear to be discrete enzymes, not dissociated into lower molecular weight agarases under fully reducing conditions, determined by comparison of silver stained native-PAGE to fully reducing SDS-PAGE and Western blots of both of gels probed with anti-agarases antiserum.

The addition of β-mercaptoethanol rendered the agarases inactive, suggesting that the agarase(s) have a disulfide bond essential for enzymatic activity. Boiling also resulted in inactivation. Antiserum, raised against the 98 kDa agarase, was cross reactive with the homologous and two other Microbulbifer 2–40 agarases, suggesting that these enzymes share common epitopes. As determined for other agarases synthesized by a given species, the cross reactivity of the different Microbulbifer 2–40 agarases with the antiserum may be attributed to common domains either in the substrate binding or active sites (Malmqvist, 1978). This anti-agarase antibody inhibited up to 71% of agarase activity in partially purified preparations , suggesting that the antibody binds directly to a common domain in the agarases active site or elsewhere on the enzyme to sterically hinder it from degrading its substrate. However, Microbulbifer 2–40 agarase is not immunologically related to *P. atlantica* agarase, since antiserum raised against either agarase was not cross reactive.

Extracellular chitinase production. Microbulbifer 2–40 attaches to chitin, and agar. Such attachment is a common mechanism used by numerous microorganisms for ICP hydrolysis (Svitil et al., 1997; Montgomery & Kirchman, 1993; Miron & Ben-Ghedalia, 1993; Haack & Breznak, 1993). This is an efficient degradative mechanism, especially for marine bacteria, maintaining contact between the organism, its enzymes and the substrate, and the end products. Also, the carbohydrases would not be so vulnerable to proteolysis, "poisoning", or dilution (Montgomery & Kirchman, 1993; Svitil et al., 1997).

Four predominant extracellular chitinases, 200, 98, 66, & 52.5 kDa, are synthesized by Microbulbifer 2–40 when cultured in chitin MM. As reported for Microbulbifer 2–40 agarases and other insoluble complex polysaccharides (ICP) degradative systems, microorganisms commonly synthesize several enzymes with like activity to degrade ICP substrates. This is also the case for bacterial production of chitinases (Harman et al., 1993; Ilyina et al., 1995; Wantabee et al., 1992 & 1990; Techkarnijanaruk et al., 1997; Bassler et al., 1991b; Vionis et al., 1996). These individual enzymes may be the result of bacterial processing of a single chitinase, smaller proteolytic degradative products of a single genetically encoded enzyme, or they may actually be unique enzymes, each encoded by an individual gene (Techkarnijanaruk et al., 1997; Wantabe et al., 1992 & 1990; Keyhani et al., 1996; Harman et al., 1993). Like agarases, Microbulbifer 2–40 chitinases appear to be individual enzymes, not concatamers of one another. This was determined by comparison of silver stained native-PAGE to fully-reducing SDS-PAGE and Western blots of both gels probed with anti-chitinase antibody.

The 98 kDa chitinase was selected as the antigen for polyclonal antibody production. The homologous chitinase, as well as 3 immunogically related chitinases, were identified by the antibody. Serological cross reactivity may result from these chitinases sharing common domains for substrate binding or hydrolysis. This has been shown for other bacterial chitinases by sequence homology and immunological cross reactivity (Robbins et al., 1992; S. Roseman, personal communication). Additionally, the antiserum inhibited 64% of Microbulbifer 2–40 chitinase activity, under experimental conditions used. Microbulbifer 2–40 chitinase does not appear to share antigenically-related domains with *V. harveyi* chitinase, since antiserum raised against *V. harveyi* chitinase is not reactive against any Microbulbifer 2–40 chitinases.

An important control showed that the anti-chitinase serum did not react with any proteins of glucose grown cells. This confirms the chitinase zymograms , showing that chitinase activity is repressed by glucose.

Example 3
Production of Filamentous Tubules

Morphogenesis in sole and multiple carbon source MM.

Microbulbifer 2–40 cells grown in glucose MM have smooth surfaces during early logarithmic phase growth. Bleb-like vesicles were formed during mid-log through stationary culture phases. Vesicles were formed due to separation of the inner and outer membrane of the cell. (These vesicles eventually partition from the cell body being released in late culture stages). During late culture phases in glucose MM, late stationary to death phase, an abundance of long, filamentous tubules; coated with small nodules, were synthesized. The tubules were –20–50 nm in diameter and their length extended up to several micrometers. The nodules have an approximate diameter of 20–40 nm.

In addition to degradosomes, filamentous tubules and bleb-like vesicles were produced during logarithmic phase growth in MM containing agar or chitin. The appearance and abundance of tubules and blebs during early growth stages in ICP were similar to those produced during late culture phase in glucose MM.

A reduction in cell size was observed during growth in MM containing ICP or in late culture stages in glucose MM.

Typical rod shaped cells, on average 1.0 μm×2.5 μm, become more stubby and more coccoid, approximately 0.5 μm×0.35 μm. The appearance of such cells correlated to with agarase or chitinase activity.

Morphogenesis of Microbulbifer 2–40 during batch growth in neoagarohexose. Microbulbifer 2–40 grown in 0.2% neoagarohexose had a generation time of 1.5 hours and reached a maximum cell density of 2.8×10$^9$ cfu/ml, following inoculation with carbohydrase-uninduced cells (glucose grown). Cell-associated agarase activity commenced at the onset of logarithmic phase at 5 hours of growth, peaking at 9 hours. Thereafter, for the next 22 hours, cell-associated agarase activity declined to almost undetectable levels, while extracellular agarase activity steadily increased. Neoagarohexose induced agarase, 575μg/ml reducing sugar equivalents, during log phase growth at levels consistent with those induced by agarose (Table 4). Cells used to inoculate neoagarohexose MM were carbohydrase-uninduced, typical in appearance (rods approximately 2.0× 0.5 μm on average), and their surfaces were smooth, lacking degradosomes. However, some tubules were transferred from washed, glucose-grown inoculum.

By early-log phase, cell surfaces were coated with vesicles, approximately 25–100 vesicles per cell of 50–500 nm, similar to cells grown in ICP. Also at this stage, coccoid cells, approximately 120–180 nm in diameter, formed at the poles of the rod-shaped cells. By mid- to late-log phase, cell surfaces are coated with tubules and vesicles and the culture contained approximately 85% coccoid cells. The rod-shaped cells released vesicles. By mid-stationary phase, the coccoid cells, coated with tubules, constituted approximately 98% of the population.

Immunoprobing of tubules. To investigate tubules and whether they contain degradative enzyme(s), antiserum was raised against Microbulbifer 2–40 LPS and was tested in ELISA, Eastern blotting, and LPS stained polyacrylamide gels to confirm its reactivity against the antigen. The antiserum was not cross reactive with control LPS, isolated from *S. typhimurium*.

TABLE 4

Highest relative carbohydrase activity in culture supernatants of 2–40 grown in complex and simple carbohydrate sole carbon substrates[a].

| Substrate | Carbohydrase Activity (μg/ml reducing sugar) | | | | | | | | | |
|---|---|---|---|---|---|---|---|---|---|---|
| | Agarase | Alginase | Amylase | CMCase[b] | Carrageenanase | Chitinase[c] | Laminarinase | Pectinase | Pullulanse | Xylanase |
| Glucose | 143 | 83 | 814 | 31 | 55 | 16 | 24 | 0 | 3 | 8 |
| Agarose | 525 | 194 | 805 | 251 | 101 | 0 | 134 | 36 | 311 | 46 |
| Alginic Acid | 230 | 633 | 419 | 20 | 97 | 0 | 109 | 0 | 59 | 50 |
| CMC[d] | 37 | 27 | 35 | 352 | 0 | 0 | 0 | 34 | 0 | 81 |
| Carrageenan | 47 | 5 | 309 | 0 | 209 | 0 | 31 | 128 | 4 | 59 |
| Chitin | 244 | 0 | 823 | 168 | 0 | 244 | 211 | 0 | 615 | 3 |
| Galactose | 46 | 0 | 15 | 0 | 0 | 31 | 63 | 0 | 27 | 0 |
| Glucan | 110 | 0 | 764 | 165 | 0 | 0 | 268 | 100 | 714 | 162 |
| Glucosamine | 142 | 56 | 0 | 0 | 0 | 0 | 54 | 0 | 0 | 0 |
| Laminarin | 61 | 0 | 589 | 27 | 0 | 0 | 1046 | 0 | 0 | 0 |
| NAG[e] | 144 | 81 | 744 | 0 | 0 | 0 | 16 | 0 | 0 | 0 |
| Pectin | 67 | 18 | 510 | 38 | 0 | 11 | 99 | 405 | 50 | 67 |
| Pullulan | 172 | 0 | 730 | 15 | 0 | 0 | 0 | 0 | 362 | 0 |
| Starch | 311 | 227 | 812 | 113 | 55 | 0 | 40 | 0 | 41 | 0 |
| Xylan | 273 | 72 | 97 | 97 | 0 | 0 | 115 | 9 | 0 | 358 |
| Xylose | 285 | 662 | 542 | 21 | 0 | 0 | 0 | 0 | 0 | 0 |

[a]Supernatants were harvested from 2–40 (grown in minimal media containing 0.2% of the respective substrate) during late logarithmic or early stationary phase. The fractions were assayed for the respective carbohydrase activity (μg/ml reducing sugar) with the DNSA reducing sugar assay.
[b]CMCase = Carboxymethyl cellulase
[c]This assay showed that chitinase was induced at low levels by chitin and at high levels by it's oligosaccharide degradation products.
[d]CMC = Carboxymethyl cellulose
[e]NAG = N-acetyl-D-glucosamine

TABLE 5

Highest relative units of carbohydrase activity in culture supernatants of 2–40 grown in complex and simple carbohydrate sole carbon substrates[a].

| Substrate | Carbohydrase Activity in Units (μg reducing sugar/μg protein[b]) | | | | | | | | | |
|---|---|---|---|---|---|---|---|---|---|---|
| | Agarase | Alginase | Amylase | CMCase[c] | Carrageenanase | Chitinase[d] | Laminarinase | Pectinase | Pullulanse | Xylanase |
| Glucose | 1.0 | 0.5 | 6.2 | 0.2 | 0.4 | 0.1 | 0.2 | 0 | 0 | 0 |
| Agarose | 7.2 | 2.7 | 9.0 | 3.4 | 1.4 | 0 | 1.5 | 0.4 | 10.0 | 0.5 |
| Alginic Acid | 1.4 | 4.1 | 2.6 | 0.1 | 0.6 | 0 | 0.8 | 0 | 0.3 | 0.3 |
| CMC[e] | 0.3 | 0.2 | 0.3 | 2.6 | 0 | 0 | 0 | 0.3 | 0 | 0.6 |
| Carrageenan | 0.4 | 0 | 2.7 | 0 | 1.9 | 0 | 0.3 | 1.2 | 0 | 0.6 |
| Chitin | 2.2 | 0 | 5.4 | 1.1 | 0 | 3.6 | 1.4 | 0 | 4.0 | 0 |
| Galactose | 0 | 0 | 0 | 0 | 0 | 0 | 0 | 0 | 0 | 0 |
| Glucan | 1.3 | 0 | 10.2 | 2.2 | 0 | 0 | 3.1 | 1.3 | 9.5 | 0 |
| Glucosamine | 2.2 | 0.7 | 0 | 0 | 0 | 0 | 0.7 | 0 | 0 | 0 |
| Laminarin | 0.6 | 0 | 5.6 | 0.3 | 0 | 0 | 9.9 | 0 | 0 | 0 |

TABLE 5-continued

Highest relative units of carbohydrase activity in culture supernatants of 2–40 grown in complex and simple carbohydrate sole carbon substrates[a].

| Substrate | Carbohydrase Activity in Units ($\mu$g reducing sugar/$\mu$g protein[b]) | | | | | | | | | |
|---|---|---|---|---|---|---|---|---|---|---|
| | Agarase | Alginase | Amylase | CMCase[c] | Carrageenanase | Chitinase[d] | Laminarinase | Pectinase | Pullulanse | Xylanase |
| NAG[f] | 1.3 | 0.8 | 6.1 | 0 | 0 | 0 | 0.1 | 0 | 0 | 0 |
| Pectin | 0.4 | 0.1 | 3.0 | 0.2 | 0 | 0 | 0.6 | 2.4 | 0.1 | 0.4 |
| Pullulan | 2.7 | 0 | 9.8 | 0.2 | 0 | 0 | 0 | 0 | 4.9 | 0 |
| Starch | 2.0 | 1.3 | 4.0 | 0.7 | 0.3 | 0 | 0.2 | 0 | 3.2 | 0 |
| Xylan | 2.7 | 0.8 | 0.7 | 1.1 | 0 | 0 | 1.0 | 0.1 | 0 | 3.3 |
| Xylose | 1.6 | 3.7 | 2.1 | 0 | 0 | 0 | 0 | 0 | 0 | 0 |

[a]Supernatants were harvested from 2–40 (grown in minimal media containing 0.2% of the respective substrate) during late logarithmic or early stationary phase. The fractions were assayed for the respective carbohydrase activity ($\mu$g/ml reducing sugar) with the DNSA reducing sugar assay.
[b]Total sample protein was determined using the Pierce BCA assay. Units of activity were calculated by dividing the total enzymatic activity ($\mu$g/ml reducing sugar) by the total sample protein ($\mu$g/ml protein).
[c]CMCase = Carboxymethyl cellulase
[d]This assay showed that chitinase was induced at low levels by chitin and at high levels by chito-oligosaccharides.
[e]CMC = Carboxymethyl cellulose
[f]NAG = N-acetyl-D-glucosamine Microbulbifer 2–40 whole cells, grown in 0.2% glucose or agarose MM, were labeled with the anti-LPS antibody. Tubules, produced during mid-log phase of growth in agarose MM, were also labeled with the anti-LPS antibody. Pre-immune serum did not label the tubules in agarose or late stage glucose cultures.

Additionally, cells grown to mid-log phase, in either agarose or chitin MM, were labeled with antiserum raised against the homologous carbohydrase. Tubules produced during growth in agarose were labeled with anti-agarase antibody. Cells and tubules produced during growth in chitin MM were not labeled by the anti-agarase antibody. Similarly, tubules produced during growth in chitin were labeled with anti-chitinase antibody. Cells and tubules produced during growth in agarose MM were not labeled by anti-chitinase antibody. Additionally, the circular nodules, attached to the tubules or released into the cultures, were labeled by anti-LPS, -agarase, and -chitinase in the respective cultures.

From these data, we conclude that the tubules are membraneous and contain carbohydrases, specifically agarase or chitinase.

Production of tubules and blebs during growth in ICP or simple sugars. 2 Microbulbifer 2–40 produces tubular extensions from the outer membrane. The filamentous tubules are –30–60 nm in diameter and reach lengths up to several micrometers. They are produced during late culture phases in glucose MM, during logarithmic growth in MM containing ICP or neoagarohexose as carbon source(s), and in mid- to late-log phase growth in MM containing both glucose and ICP(s). These tubules are membranous and localize agarase (s) or chitinase(s), as determined by immunoelectron microscopy. They appear to elongate directly from the degradosome structures and their abundance increases with the culture duration, comprising a substantial amount of the cell mass. "Nodules" are random on the surface of these tubules and also free in the culture. They also package agarases or chitinases.

Purification of Tubules. The cell media is centrifuged at 6000 rpm for 10 minutes to pellet the cells. The supernatant is then filtered through filter paper with a pore size of 2–10 $\mu$m. The tubules are retained by the filter paper and thus can be removed from the surface of the filter paper. After the tubules are purified in this manner, they can be used without further purification to degrade insoluble complex polysaccharides.

Example 4
Partial Purification of Microbulbifer 2–40 Alginase

2–40 alginases were harvested from 28 hour culture supernatant of Microbulbifer 2–40 grown in 0.2% alginic acid minimal media. Maximum alginase activity was found in early stationary phase spent media, consistent with other Microbulbifer 2–40 carbohydrases. The supernatant was concentrated using the Minitan tangential flow apparatus and the enzymes precipitated with 70% ammonium sulfate. Preliminary ammonium sulfate precipitations of 20, 30, 40, 50, 60, 70, 80% were tested and it was found that maximum alginase activity was present in the 70% fraction. The ammonium sulfate was dialyzed out with 20 mM Pipes at 4° C., then further concentrated using tentriprep.

Zymograms. The recovered alginases were analyzed by native-PAGE 8% and alginase activity was determined by zymorgram gel overlays containing 0.1% alginic acid. Following overnight incubation in 20 mM Pipes buffer at 37° C., the activity bands were visualized by staining with 0.08% toluidine blue-O in 7% glacial acetic acid, which binds the non-degraded alginic acid.

Identification of multiple alginases from Microbulbifer 2–40 by native-PAGE (A) Silver stain of 8% native-PAGE and (B) corresponding zymogram of 8% native-PA gel overlay with molecular weights added for reference. FIG. 7, for both A and B Lane 1, 60 $\mu$g total protein of 0.2% glucose grown 2–40; Lane 2, 40 $\mu$g total protein of partially purified concentrated alginase preparations. Duplicate lanes of glucose Microbulbifer 2–40 cell prep and alginase prep from the gel were (A) silver stained and (B) used in the zymogram overlay, then stained with toluidine blue 0. There are eight bands with alginase activity with approximate molecular weight of 87, 66, 43, 39, 35, 27, 25 and 23 kD.

Example 5
Degradation of Pseudomonas Biofilms
Strains:
a) Microbulbifer 2–40
b) *Pseudomonas aeruginosa* 2–40 FRD1 (Mucoid cystic fibrosis isolate) *Pseudomonas aeruginosa* FRD462 (polymannuronicacid producing mutant) (J. Bact 172:2894–2900).

Biomass. One liter of Microbulbifer 2–40 was grown to late log phase ($10^9$ cells $ml^{-1}$), harvested, brought up in 2% instant ocean (IO) and seeded onto moist biofilms of Pseudomonas aeruginosa FRD1 & 462. (Grown on nutrient broth+0.5% yeast extract with the spent medium decanted.) Microbulbifer 2–40 was incubated at 30° C. with biofilms over a time course of seven days.

Biofilm degradation. This was monitored visually by examination of the film and by the elaboration of reducing sugars (glucuronic and mannuronic acids). Following the procedures of the above examples. Background counts of biofilms of Pseudomonas aeruginosa that were not exposed to Microbulbifer 2–40 were subtracted from the experimental samples. The results are shown in the following table.

TABLE 6

| P. aeruginosa strain | Days & pg reducing sugar $ml^{-1}$ | | | |
|---|---|---|---|---|
| | 0 | 1 | 3 | 7 |
| FRD1 | 0 | 11 | 48 | 192 |
| FRD462 | 0 | 6 | 70 | 101 |

FDR1, & to a lesser extent FRD462, biofilms were visibly less obvious after 7 days when exposed to induced Microbulbifer 2–40 then when exposed to sterile IO.

Example 6

Production of S. mutans Biofilm Degrading Enzyme Mixtures

Strains a) Microbulbifer 2–40 b) Streptococcus mutans ATTC 25175 (type strain)

Biomass. Microbulbifer 2–40 cells are grown in broth to late log phase ($10^9$ cells $ml^{-1}$), harvested, brought up in 2% instant ocean (IO) and seeded onto moist biofilms of Streptococcus mutans, (S. mutans is grown on trypticase soy agar with 5% defibrinated sheep blood at 37° C.) Microbulbifer 2–40 is incubated at 30° C. with the biofilms in time course.

Biofilm degradation. Biofilm degradation is monitored visually by examination of the film and by the elaboration of reducing sugars. Following the procedures of the above examples, biofilms of Streptococcus mutans that are not exposed to Microbulbifer 2–40 and the enzymes it produces are utilized as control materials.

What is claimed is:

1. A method for the preparation of multiple-specificity hydrolytic enzyme mixtures, comprising the steps of:
    a) culturing a bacterial strain in a culture medium or series of media containing more than one polysaccharide present in a targeted biofilm, or a derivative thereof, as a primary carbon source to support growth and metabolism of the bacterial strain, wherein said bacterial strain grows on and catabolizes or degrades one or more complex polysaccharide sources; and
    b) separating any multiple-specificity, hydrolytic enzyme mixtures produced by said bacterial strain from the culture medium, wherein said hydrolytic enzyme mixtures are produced by the bacterial strain in degradosomes, tubules, vesicles or a combination of degradosomes, tubules or vesicles.

2. The method according to claim 1, wherein said bacterial strain is a marine saprophytic bacterium.

3. The method according to claim 2, wherein said bacterial strain is a Microbulbifer or a Marinobacterium.

4. The method according to claim 2, wherein said bacterial strain is selected from the group consisting of 2–40, Microbulbifer IRE-31 and Marinobacterium KW-40.

5. The method according to claim 4, wherein said bacterial strain is 2–40.

6. A method for improving the treatment of Pseudomonas aeruginosa infection in a patient in need of such treatment, comprising administering a multiple-specificity hydrolytic enzyme mixture or a component thereof which degrades alginate to said patient, wherein said hydrolytic enzyme mixtures are produced by a bacterial strain in degradosomes, tubules, vesicles or a combination of degradosomes, tubules or vesicles, said bacterial strain cultured in a culture medium or series of media containing more than one polysaccharide present in a targeted biofilm.

7. The method according to claim 6, wherein said multiple-specificity hydrolytic enzyme mixture is produced by the following steps:
    a) culturing Microbulbifer or Marinobacterium in a culture medium or series of media containing alginate as a primary carbon source to support any growth and metabolism of Microbulbifer or Marinobacterium; and
    b) separating any multiple-specificity, hydrolytic enzyme mixture and any degradosomes, tubules, vesicles or a combination of degradosomes, tubules or vesicles produced by Microbulbifer or Marinobacterium from the culture medium.

8. The method according to claim 6, bacterial strain is 2–40.

9. The method according to claim 6, wherein said Pseudomonas aeruginosa infection is associated with cystic fibrosis.

10. The method according to claim 9, wherein said multiple-specificity, hydrolytic enzyme mixture is administered to said patient's lungs.

11. The method according to claim 10, wherein said multiple-specificity, hydrolytic enzyme mixture is administered to said patient along with an antibiotic, a DNase, a protease inhibitor or both a DNase and a protease inhibitor.

12. The method according to claim 6, wherein said Pseudomonas aeruginosa infection is associated with a burn wound.

13. A method for degrading biofilms on an oral surface, comprising applying a multiple-specificity, hydrolytic enzyme mixture or a component thereof to said oral surface, wherein said hydrolytic enzyme mixture is produced by a bacterial strain in degradosomes, tubules, vesicles or a combination of degradosomes, tubules or vesicles, said bacterial strain cultured in a culture medium or series of media containing more than one polysaccharide present in the biofilm.

14. A method for degrading biofilms on an oral surface, comprising applying a multiple-specificity, hydrolytic enzyme mixture or a component thereof to said oral surface, wherein said hydrolytic enzyme mixture is contained in or isolated from culture media and degradosomes, tubules, vesicles or a combination of degradosomes, tubules or vesicles produced by a bacterial strain.

15. The method according to claim 14, wherein said multiple-specificity, hydrolytic enzyme mixture is produced by the following steps:
    a) culturing Microbulbifer or Marinobacterium in a culture medium or series of media containing polysaccharides produced by Streptococcus mutans, as a primary carbon source to support growth and metabolism of Microbulbifer or, Marinobacterium; and
    b) separating any multiple-specificity, hydrolytic enzyme mixture produced by Microbulbifer or Marinobacterium from the culture medium.

16. The method according to claim 14, wherein said bacterial strain is 2–40.

17. The method according to claim 14, wherein said multiple-specificity, hydrolytic enzyme mixture is administered in combination with an abrasive.

18. The method according to claim 14, wherein said multiple-specificity, hydrolytic enzyme mixture degrades biofilms associated with dental caries.

19. The method according to claim 14, wherein said multiple-specificity, hydrolytic enzyme mixture degrades biofilms associated with periodontal disease.

20. A method for reducing biofilm formation on an implantable medical device, comprising applying a multiple-specificity, hydrolytic enzyme mixture or a component thereof to the surface of said device, wherein said multiple-specificity, hydrolytic enzyme mixture is produced by Microbulbifer or Marinobacterium.

21. A method for reducing biofilm formation on an industrial surface, comprising the steps of:
   a) culturing a bacterial strain in a culture medium or series of media containing at least two polysaccharides present in a targeted biofilm, or a derivative thereof, as primary carbon sources to support growth and metabolism of the bacterial strain, wherein said bacterial strain grows on and catabolizes or degrades two or more complex polysaccharide sources;
   b) separating any multiple-specificity, hydrolytic enzyme mixtures produced by said bacterial strain from the culture medium, and
   c) applying said multiple-specificity, hydrolytic enzyme mixture or a component thereof to said industrial surface.

22. The method according to claim 21, wherein said multiple-specificity, hydrolytic enzyme mixture is isolated from the culture medium and from degradosomes, tubules, vesicles or a combination of degradosomes, tubules or vesicles.

23. The method according to claim 21, wherein said bacterial strain is a marine saprophytic bacterium.

24. The method according to claim 23, wherein said bacterial strain is a Microbulbifer or a Marinobacterium.

25. The method according to claim 23, wherein said bacterial strain is selected from the group consisting of 2–40, Microbulbifer IRE-31 and Marinobacterium KW-40.

26. The method according to claim 25, wherein said bacterial strain is 2–40.

27. A method for the preparation of biofilm-degrading, purified hydrolytic enzymes, comprising the steps of:
   a) culturing a bacterial strain in a culture medium or series of media containing more than one polysaccharide present in a targeted biofilm, as a primary carbon source to support growth and metabolism of the bacterial strain, wherein said bacterial strain grows on and catabolizes or degrades a wide range of complex polysaccharide sources; and
   b) separating any multiple-specificity, hydrolytic enzyme mixtures produced by said bacterial strain from the culture medium, wherein said hydrolytic enzyme mixtures are produced by the bacterial strain in degradosomes, tubules, vesicles or a combination of degradosomes, tubules or vesicles; and
   c) purifying at least one specific enzyme from the multiple-specificity, hydrolytic enzyme mixture, wherein the purified enzyme degrades at least one polysaccharide component of the targeted biofilm.

28. A method for the preparation of biofilm-degrading, purified hydrolytic enzymes, comprising the steps of:
   a) culturing a bacterial strain in a culture medium or series of media containing at least two polysaccharides which are present in a targeted biofilm, as primary carbon sources to support growth and metabolism of the bacterial strain, wherein said bacterial strain grows on and catabolizes or degrades a wide range of complex polysaccharide sources;
   b) isolating any multiple-specificity, hydrolytic enzyme mixture produced by said bacterial strain from the culture medium and from degradosomes, tubules, vesicles or a combination of degradosomes, tubules or vesicles produced by the bacterial strain; and
   c) purifying at least one specific enzyme from the multiple-specificity, hydrolytic enzyme mixture, wherein the purified enzyme degrades at least one polysaccharide component of the targeted biofilm.

29. The method according to claim 28, wherein said bacterial strain is Microbulbifer or Marinobacterium.

30. A method for reducing biofilms on a targeted surface, comprising applying living Microbulbifer, Marinobacterium or a related organism in such a manner that it contacts said targeted surface.

31. The method according to claim 30, wherein said organism is 2–40.

32. A method for degrading biofilms on a contact lens, comprising applying a multiple-specificity, hydrolytic enzyme mixture produced by Microbulbifer, Marinobacterium or a related organism to said contact lens.

33. The method according to claim 31, wherein said multiple-specificity, hydrolytic enzyme mixture is produced by the following steps:
   a) culturing Microbulbifer or Marinobacterium in a culture medium or series of media containing at least two polysaccharides produced by bacteria found on contact lenses, as a primary carbon source to support growth and metabolism of Microbulbifer or Marinobacterium; and
   b) isolating any multiple-specificity, hydrolytic enzyme mixture produced by Microbulbifer or Marinobacterium from the culture medium and from degradosomes, tubules, vesicles or a combination of degradosomes, tubules or vesicles produced by Microbulbifer or Marinobacterium.

34. The method according to claim 32, wherein said bacterial strain is 2–40.

35. The method according to claim 27, wherein said multiple-specificity, hydrolytic enzyme mixture is isolated from the culture medium and from degradosomes, tubules, vesicles or a combination of degradosomes, tubules or vesicles.

* * * * *